(12) United States Patent
Chen et al.

(10) Patent No.: US 8,603,483 B2
(45) Date of Patent: Dec. 10, 2013

(54) ANTI-INTEGRIN IMMUNOCONJUGATES, METHODS AND USES

(75) Inventors: Qiming Chen, Collegeville, PA (US);
Mohit Trikha, San Mateo, CA (US);
Robert J. Lutz, Wayland, MA (US);
Rita M. Steeves, Stoneham, MA (US);
Godfrey Amphlett, Cambridge, MA (US)

(73) Assignees: Janssen Biotech, Inc., Radnor, PA (US); Immunogen, Inc., Cambridge, MA (US)

( * ) Notice: Subject to any disclaimer, the term of this patent is extended or adjusted under 35 U.S.C. 154(b) by 0 days.

(21) Appl. No.: 11/290,249

(22) Filed: Nov. 30, 2005

(65) Prior Publication Data
US 2006/0127407 A1 Jun. 15, 2006

Related U.S. Application Data

(60) Provisional application No. 60/634,445, filed on Dec. 9, 2004.

(51) Int. Cl.
*C07K 16/00* (2006.01)
*C07K 17/06* (2006.01)
*A61K 39/44* (2006.01)

(52) U.S. Cl.
USPC .............. 424/181.1; 530/391.1; 530/391.5; 530/391.7; 530/391.9; 530/402; 530/403; 530/404

(58) Field of Classification Search
None
See application file for complete search history.

(56) References Cited

U.S. PATENT DOCUMENTS

| | | | |
|---|---|---|---|
| 5,208,020 A | 5/1993 | Chari et al. | |
| 5,855,866 A | 1/1999 | Thorpe et al. | |
| 6,051,230 A | 4/2000 | Thorpe et al. | |
| 6,570,024 B2 | 5/2003 | Eldridge et al. | |
| 6,913,748 B2 | 7/2005 | Widdison | |
| 7,163,681 B2 * | 1/2007 | Giles-Komar et al. | 424/144.1 |
| 7,288,390 B2 * | 10/2007 | Heavner et al. | 435/69.1 |
| 7,374,762 B2 * | 5/2008 | Amphlett et al. | 424/184.1 |
| 2002/0197261 A1 | 12/2002 | Li et al. | |
| 2003/0040044 A1 | 2/2003 | Trikha et al. | |
| 2003/0103985 A1 * | 6/2003 | Adolf et al. | 424/178.1 |
| 2004/0185507 A1 | 9/2004 | Trikha et al. | |
| 2004/0235840 A1 * | 11/2004 | Chari et al. | 514/229.5 |

FOREIGN PATENT DOCUMENTS

| | | |
|---|---|---|
| EP | 0 425 235 | 5/1991 |
| JP | 3161490 | 7/1991 |
| WO | WO 00/31248 A | 6/2000 |
| WO | WO 00/64480 | 11/2000 |
| WO | WO 01/00244 | 1/2001 |
| WO | WO 02/12501 | 2/2002 |
| WO | WO 02/012501 A3 | 2/2002 |
| WO | WO 02/094325 | 11/2002 |
| WO | WO 02/094325 A2 * | 11/2002 |
| WO | WO 02/098883 * | 12/2002 |
| WO | WO 2004/103272 A2 | 12/2004 |
| WO | WO 2006/062779 A2 * | 6/2006 |

OTHER PUBLICATIONS

Trikha et al (AACR Abstract # 754, Jul. 2003).*
Chen et al. αv Integrin-Targeted Immunoconjugates Regress Established Human Tumors in Xenograft Models. Clin Cancer Res, 2007. 13(12): 3689-95.*
International Preliminary Report on Patentability from International Application No. PCT/US2005/043250, Anti-Integrin Immunoconjugates, Methods and Uses, dated Dec. 17, 2007.*
International Search Report from International Application No. PCT/US2005/043250, Anti-Integrin Immunoconjugates, Methods and Uses; Dated May 24, 2006.*
Eliceiri, B P. and Cheresh, D.A., "The role of αv integrins during angiogenesis: insights into potential mechanisms of action and clinical development," J. Clin. Inv., 103(9): 1227-1230 (1999).*
Cassady et al, "Recent Developments int eh Maytansinoid Antitumore Agents", Chem. Pharm Bull, 2004, pp. 1-26, vol. 52 (1).
Chari et al, "Immunoconjugates containing novel maytansinoids: promising anticancer drugs" Cancer Research, 1992, pp. 127-131, vol. 52 (1).
Kreitman et al, "Targeting growth factor receptors with fusion toxins" Internat. J. Immunopharm, 1992, pp. 465-472, vol. 14 (3)
Pastan et al, "Immunotoxins" Cell, 1986, pp. 641-648.
Thorpe, PE et al, "New coupling agents for the synthesis of immunotoxins containing a hindered disulfide bond with improved stability in vivo." Cancer Res. 1987, pp. 5924-5931, 47 (22).
Trikha et al, "CNTO 95, a fully human monoclonal antibody that inhibits v integrins, has antitumor and antiangiogenic activity in vivo." Int. J. Cancer, 2004, pp. 326-333, 110 (3).
Devita et al, "Principles and practices of oncology." Cancer, 2001, 6th edition, Philadelphia: J. B. Lippincott Company.
Kawai et al, "Chemical modification of ansamitocins III, Synthesis and biological effects of 3-acyl esters of maytansinaol." Chem Pharm Bull ) 1984, pp. 3441-3451, vol. 32.
Chari et al, "Targeted delivery of chemotherapeutics: tumor-activated prodrug therapy." Adv. Drug Delivery Rev. 1998, pp. 89-104, vol. 31.
Liu et al, "Eradication of large colon tumor xenografts by targeted delivery of maytansinoids." Pro. Natl., Acad Sci, USA, 1996, pp. 8619-8623, vol. 93.
Chari et al, "Enhancement of the Selectivity and Antitumor Efficacy of a CC-1065 Analog through Immunoconjugate Formation." Cancer Res. 1995, pp. 4079-4084, vol. 55.

(Continued)

Primary Examiner — Maher Haddad
(74) Attorney, Agent, or Firm — Hamilton, Brook, Smith & Reynolds, P.C.

(57) ABSTRACT

The invention relates to conjugates of anti-integrin specific antibodies with cytotoxic compounds, the synthesis, selection, and use of such conjugates for use in cancer therapy or other diseases mediated by cell proliferation, cell migration, or inflammation and which pathology involves angiogenesis or neovascularization of new tissue. In addition the invention relates to combination therapy of such diseases wherein the treatment comprises use of said conjugates in combination with one or more other treatment modalities including but not limited to: chemotherapy, surgery or radiation therapy. The preferred conjugates contain maytansinoid compounds linked to the antibody by a disulfide linkage, and preferred chemotherapeutic agents are doxorubicin, a taxane, a camptothecin, a podophyllotoxin, a nucleoside analog, or a pyrimidine analog.

15 Claims, 15 Drawing Sheets

(56) References Cited

OTHER PUBLICATIONS

Pasqualini et al, "A study of the structure, function and distribution of beta5 integrins using novel anti-beta5 monoclonal antibodies." JCell Sci, 1993, -111, vol. 105 (pt1).

Brooks et al, "Integrin alphavbeta3 antagonists promote tumor regression by inducing apoptosis of angiogenic blood vessels." Cell 1994, pp. 1157-1164, vol. 79.

Reinmuth et al, "Alphavbeta3 integrin antagonist S247 decreases colon cancer metastasis and angiogenesis and improves survival in mice." Cancer Res. 2003, pp. 2079-2087, vol. 63.

Kumar et al, "Inhibition of angiogenesis and tumor growth by SCH221153, a dual alpha(v)beta3 and alpha(v)beta5 integrin receptor antagonist." Cancer Res 2001, pp. 2232-2238, vol. 61.

Hieken et al, "Molecular prognostic markers in intermediate-thickness cutaneous malignant melanoma." Cancer, 1999, pp. 375-382, vol. 85.

Hsu et al, "Adenoviral gene transfer of beta3 integrin subunit induces conversion from radial to vertical phase in primary human melanoma." Am J Pathol, 1998, pp. 1435-1442, vol. 153.

Brooks et al, "Insulin-like growth factor receptor cooperates with integrin alphabeta5 to promote tumor cell dissemination in vivo." J Clin Invest, 1997, pp. 1390-1398, vol. 99.

Marshall et al, "Alphavbeta1 is a receptor for vitronectin and fibrinogen, and acts with alpha5beta1 to mediate spreading on fibronectin." J Cell Sci, 1995, pp. 2241-2251, vol. 108 (pt3).

Breuss et al, "Expression of the beta6 integrin subunit in development, neoplasia and tissue repair suggests a role in epithelial remodeling." J Cell Sci, 1995, pp. 2241-2251, vol. 108(pt6).

Thomas et al, "Integrins and oral cancer." Oral Oncol., 1997, pp. 381-388, vol. 33.

Posey et al, "A pilot trial of Vitaxin, a humanized anti-vitronectin receptor (anti-alphabeta3) antibody in patients with metastatic cancer." Cancer Biother Radiopharm, 2001, pp. 125-132, vol. 16.

Patel et al, "Pilot study of Vitaxin—an angiogenesis inhibitor—in patients with advancedleiomyosarcomas." Cancer, 2001, pp. 1347-1348, vol. 92.

Eskens et al, "Phase I and pharmacokinetic study of continuous twice weekly intravenous administration of cilengitide (EMD 121974), a novel inhibitor of the integrins alphavbeta3 and alphabeta5 in patients with advanced solid tumours." Eur J Cancer, 2003, pp. 917-926, vol. 39.

Saito et al, "Drug delivery strategy utilizing conjugation via reversible disulfile linkages: role and site of cellular reducing activities," Advanced Drug Delivery Reviews, 2003, pp. 199-215, vol. 55, Elsevier.

Smith et al, "Technology evaluation: C242-DM1, ImmunoGen, Inc.," Current Opinion in Molecular Therapeutics, 2001, pp. 198-203, vol. 3 (2), Pharma Press Ltd, ISSN 1464-8431.

Helft et al, "A Phase I Study of Cantuzumab Mertansine Administered as a Single Intravenous Infusion Once Weekly in Patients with Advanced Solid Tumors," Clinical Cancer Research, 2004, pp. 4363-4368, vol. 10.

Tassone et al, "In Vitro and in Vivo Activity of the Maytansinoid Immunoconjugate huN901-$N^2$-(3-Mercapto-1-Oxopropyl)-Maytansine against $CD56^+$ Multiple Myeloma Cells," Cancer Res., 2004, pp. 4629-4636, vol. 64.

Tolcher et al, "Cantuzumab Mertansine, a Maytansinoid Immunoconjugate Directed to the CanAg Antigen: A Phase I, Pharmacokinetic, and Biologic Correlative Study," Journal of Clin Oncology, 2003, pp. 211-222, vol. 21, No. 2.

Xie et al, "Pharmacokinetics and Biodistribution of the Antitumor Immunoconjugate, Cantuzumab Mertansine (huC242-DM1), and Its Two Components in Mice," The Journal of Pharmacology and Experimental Therapeutics, 2004, pp. 1073-1082, vol. 308, The American Society for Pharmacology and Experimental Therapeutics.

Mueller, B.M. et al., "Antibody conjugates with morpholinodoxorubicin and acid-cleavable linkers," Bioconjuate Chemistry, 1(5):325-330 Sep. 1990.

* cited by examiner n ≥ 1

R₁, R₂, R₃ = H, Me, C₂H₅, linear alkyl or alkenyl having from 1 to 10 carbon atoms, branched or cyclic alkyl or alkenyl having from 3 to 10 carbon atoms, phenyl, substituted phenyl, or heterocyclic aromatic, heterocycloalkyl radical

Z = H, SR₃

DM1    n= 1, R1, R2 = H, Z = H
DM3    n= 2, R1 = H, R2 = Me, Z = H
DM4    n= 2, R1, R2 = Me, Z = H

SPDP

SPDB

SPP

SMNP

SSNPB

SSNPP

SMCC

*Fig. 3*

SEQUENCE LISTING

```
<160> NUMBER OF SEQ ID NOS: 9

<210> SEQ ID NO 1
<211> LENGTH: 5
<212> TYPE: PRT
<213> ORGANISM: Homo sapiens

<400> SEQUENCE: 1

Arg Tyr Thr Met His
1               5

<210> SEQ ID NO 2
<211> LENGTH: 17
<212> TYPE: PRT
<213> ORGANISM: Homo sapiens

<400> SEQUENCE: 2
```

```
Val Ile Ser Phe Asp Gly Ser Asn Lys Tyr Tyr Val Asp Ser Val Lys
1               5                   10                  15

Gly

<210> SEQ ID NO 3
<211> LENGTH: 10
<212> TYPE: PRT
<213> ORGANISM: Homo sapiens

<400> SEQUENCE: 3

Glu Ala Arg Gly Ser Tyr Ala Phe Asp Ile
1               5                   10

<210> SEQ ID NO 4
<211> LENGTH: 11
<212> TYPE: PRT
<213> ORGANISM: Homo sapiens

<400> SEQUENCE: 4

Arg Ala Ser Gln Ser Val Ser Ser Tyr Leu Ala
1               5                   10

<210> SEQ ID NO 5
<211> LENGTH: 7
<212> TYPE: PRT
<213> ORGANISM: Homo sapiens

<400> SEQUENCE: 5

Asp Ala Ser Asn Arg Ala Thr
1               5

<210> SEQ ID NO 6
<211> LENGTH: 8
<212> TYPE: PRT
<213> ORGANISM: Homo sapiens

<400> SEQUENCE: 6

Gln Gln Arg Ser Asn Trp Pro Pro
1               5

<210> SEQ ID NO 7
<211> LENGTH: 119
<212> TYPE: PRT
<213> ORGANISM: Homo sapiens

<400> SEQUENCE: 7

Gln Val Gln Leu Val Glu Ser Gly Gly Val Gln Pro Gly Arg
1               5                   10                  15

Ser Arg Arg Leu Ser Cys Ala Ala Ser Gly Phe Thr Phe Ser Arg Tyr
                20                  25                  30

Thr Met His Trp Val Arg Gln Ala Pro Gly Lys Gly Leu Glu Trp Val
            35                  40                  45

Ala Val Ile Ser Phe Asp Gly Ser Asn Lys Tyr Tyr Val Asp Ser Val
        50                  55                  60

Lys Gly Arg Phe Thr Ile Ser Arg Asp Asn Ser Glu Asn Thr Leu Tyr
65                  70                  75                  80

Leu Gln Val Asn Ile Leu Arg Ala Glu Asp Thr Ala Val Tyr Tyr Cys
                85                  90                  95

Ala Arg Glu Ala Arg Gly Ser Tyr Ala Phe Asp Ile Trp Gly Gln Gly
            100                 105                 110

Thr Met Val Thr Val Ser Ser
            115
```

-continued

```
<210> SEQ ID NO 8
<211> LENGTH: 108
<212> TYPE: PRT
<213> ORGANISM: Homo sapiens

<400> SEQUENCE: 8

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
            85                  90                  95

Phe Thr Phe Gly Pro Gly Thr Lys Val Asp Ile Lys
        100                 105

<210> SEQ ID NO 9
<211> LENGTH: 1048
<212> TYPE: PRT
<213> ORGANISM: Homo sapiens

<400> SEQUENCE: 9

Met Ala Phe Pro Pro Arg Arg Arg Leu Arg Leu Gly Pro Arg Gly Leu
1               5                   10                  15

Pro Leu Leu Leu Ser Gly Leu Leu Leu Pro Leu Cys Arg Ala Phe Asn
            20                  25                  30

Leu Asp Val Asp Ser Pro Ala Glu Tyr Ser Gly Pro Glu Gly Ser Tyr
        35                  40                  45

Phe Gly Phe Ala Val Asp Phe Phe Val Pro Ser Ala Ser Ser Arg Met
    50                  55                  60

Phe Leu Leu Val Gly Ala Pro Lys Ala Asn Thr Thr Gln Pro Gly Ile
65                  70                  75                  80

Val Glu Gly Gly Gln Val Leu Lys Cys Asp Trp Ser Ser Thr Arg Arg
            85                  90                  95

Cys Gln Pro Ile Glu Phe Asp Ala Thr Gly Asn Arg Asp Tyr Ala Lys
        100                 105                 110

Asp Asp Pro Leu Glu Phe Lys Ser His Gln Trp Phe Gly Ala Ser Val
    115                 120                 125

Arg Ser Lys Gln Asp Lys Ile Leu Ala Cys Ala Pro Leu Tyr His Trp
130                 135                 140

Arg Thr Glu Met Lys Gln Glu Arg Glu Pro Val Gly Thr Cys Phe Leu
145                 150                 155                 160

Gln Asp Gly Thr Lys Thr Val Glu Tyr Ala Pro Cys Arg Ser Gln Asp
            165                 170                 175

Ile Asp Ala Asp Gly Gln Gly Phe Cys Gln Gly Gly Phe Ser Ile Asp
        180                 185                 190

Phe Thr Lys Ala Asp Arg Val Leu Leu Gly Gly Pro Gly Ser Phe Tyr
    195                 200                 205

Trp Gln Gly Gln Leu Ile Ser Asp Gln Val Ala Glu Ile Val Ser Lys
210                 215                 220
```

```
Tyr Asp Pro Asn Val Tyr Ser Ile Lys Tyr Asn Asn Gln Leu Ala Thr
225                 230                 235                 240

Arg Thr Ala Gln Ala Ile Phe Asp Asp Ser Tyr Leu Gly Tyr Ser Val
            245                 250                 255

Ala Val Gly Asp Phe Asn Gly Asp Gly Ile Asp Asp Phe Val Ser Gly
        260                 265                 270

Val Pro Arg Ala Ala Arg Thr Leu Gly Met Val Tyr Ile Tyr Asp Gly
    275                 280                 285

Lys Asn Met Ser Ser Leu Tyr Asn Phe Thr Gly Glu Gln Met Ala Ala
        290                 295                 300

Tyr Phe Gly Phe Ser Val Ala Ala Thr Asp Ile Asn Gly Asp Asp Tyr
305                 310                 315                 320

Ala Asp Val Phe Ile Gly Ala Pro Leu Phe Met Asp Arg Gly Ser Asp
            325                 330                 335

Gly Lys Leu Gln Glu Val Gly Gln Val Ser Val Ser Leu Gln Arg Ala
        340                 345                 350

Ser Gly Asp Phe Gln Thr Thr Lys Leu Asn Gly Phe Glu Val Phe Ala
    355                 360                 365

Arg Phe Gly Ser Ala Ile Ala Pro Leu Gly Asp Leu Asp Gln Asp Gly
370                 375                 380

Phe Asn Asp Ile Ala Ile Ala Ala Pro Tyr Gly Gly Glu Asp Lys Lys
385                 390                 395                 400

Gly Ile Val Tyr Ile Phe Asn Gly Arg Ser Thr Gly Leu Asn Ala Val
            405                 410                 415

Pro Ser Gln Ile Leu Glu Gly Gln Trp Ala Ala Arg Ser Met Pro Pro
        420                 425                 430

Ser Phe Gly Tyr Ser Met Lys Gly Ala Thr Asp Ile Asp Lys Asn Gly
    435                 440                 445

Tyr Pro Asp Leu Ile Val Gly Ala Phe Gly Val Asp Arg Ala Ile Leu
450                 455                 460

Tyr Arg Ala Arg Pro Val Ile Thr Val Asn Ala Gly Leu Glu Val Tyr
465                 470                 475                 480

Pro Ser Ile Leu Asn Gln Asp Asn Lys Thr Cys Ser Leu Pro Gly Thr
            485                 490                 495

Ala Leu Lys Val Ser Cys Phe Asn Val Arg Phe Cys Leu Lys Ala Asp
        500                 505                 510

Gly Lys Gly Val Leu Pro Arg Lys Leu Asn Phe Gln Val Glu Leu Leu
    515                 520                 525

Leu Asp Lys Leu Lys Gln Lys Gly Ala Ile Arg Arg Ala Leu Phe Leu
530                 535                 540

Tyr Ser Arg Ser Pro Ser His Ser Lys Asn Met Thr Ile Ser Arg Gly
545                 550                 555                 560

Gly Leu Met Gln Cys Glu Glu Leu Ile Ala Tyr Leu Arg Asp Glu Ser
            565                 570                 575

Glu Phe Arg Asp Lys Leu Thr Pro Ile Thr Ile Phe Met Glu Tyr Arg
        580                 585                 590

Leu Asp Tyr Arg Thr Ala Ala Asp Thr Thr Gly Leu Gln Pro Ile Leu
    595                 600                 605

Asn Gln Phe Thr Pro Ala Asn Ile Ser Arg Gln Ala His Ile Leu Leu
610                 615                 620

Asp Cys Gly Glu Asp Asn Val Cys Lys Pro Lys Leu Glu Val Ser Val
625                 630                 635                 640

Asp Ser Asp Gln Lys Lys Ile Tyr Ile Gly Asp Asp Asn Pro Leu Thr
            645                 650                 655
```

-continued

```
Leu Ile Val Lys Ala Gln Asn Gln Gly Glu Gly Ala Tyr Glu Ala Glu
            660                 665                 670

Leu Ile Val Ser Ile Pro Leu Gln Ala Asp Phe Ile Gly Val Val Arg
            675                 680                 685

Asn Asn Glu Ala Leu Ala Arg Leu Ser Cys Ala Phe Lys Thr Glu Asn
690                 695                 700

Gln Thr Arg Gln Val Val Cys Asp Leu Gly Asn Pro Met Lys Ala Gly
705                 710                 715                 720

Thr Gln Leu Leu Ala Gly Leu Arg Phe Ser Val His Gln Gln Ser Glu
            725                 730                 735

Met Asp Thr Ser Val Lys Phe Asp Leu Gln Ile Gln Ser Ser Asn Leu
            740                 745                 750

Phe Asp Lys Val Ser Pro Val Val Ser His Lys Val Asp Leu Ala Val
            755                 760                 765

Leu Ala Ala Val Glu Ile Arg Gly Val Ser Ser Pro Asp His Ile Phe
            770                 775                 780

Leu Pro Ile Pro Asn Trp Glu His Lys Glu Asn Pro Glu Thr Glu Glu
785                 790                 795                 800

Asp Val Gly Pro Val Val Gln His Ile Tyr Glu Leu Arg Asn Asn Gly
            805                 810                 815

Pro Ser Ser Phe Ser Lys Ala Met Leu His Leu Gln Trp Pro Tyr Lys
            820                 825                 830

Tyr Asn Asn Asn Thr Leu Leu Tyr Ile Leu His Tyr Asp Ile Asp Gly
            835                 840                 845

Pro Met Asn Cys Thr Ser Asp Met Glu Ile Asn Pro Leu Arg Ile Lys
850                 855                 860

Ile Ser Ser Leu Gln Thr Thr Glu Lys Asn Asp Thr Val Ala Gly Gln
865                 870                 875                 880

Gly Glu Arg Asp His Leu Ile Thr Lys Arg Asp Leu Ala Leu Ser Glu
            885                 890                 895

Gly Asp Ile His Thr Leu Gly Cys Gly Val Ala Gln Cys Leu Lys Ile
            900                 905                 910

Val Cys Gln Val Gly Arg Leu Asp Arg Gly Lys Ser Ala Ile Leu Tyr
            915                 920                 925

Val Lys Ser Leu Leu Trp Thr Glu Thr Phe Met Asn Lys Glu Asn Gln
930                 935                 940

Asn His Ser Tyr Ser Leu Lys Ser Ser Ala Ser Phe Asn Val Ile Glu
945                 950                 955                 960

Phe Pro Tyr Lys Asn Leu Pro Ile Glu Asp Ile Thr Asn Ser Thr Leu
            965                 970                 975

Val Thr Thr Asn Val Thr Trp Gly Ile Gln Pro Ala Pro Met Pro Val
            980                 985                 990

Pro Val Trp Val Ile Ile Leu Ala Val Leu Ala Gly Leu Leu Leu Leu
            995                 1000                1005

Ala Val Leu Val Phe Val Met Tyr Arg Met Gly Phe Phe Lys Arg
            1010                1015                1020

Val Arg Pro Pro Gln Glu Glu Gln Glu Arg Glu Gln Leu Gln Pro
            1025                1030                1035

His Glu Asn Gly Glu Gly Asn Ser Glu Thr
            1040                1045
```

ANTI-INTEGRIN IMMUNOCONJUGATES, METHODS AND USES

CROSS REFERENCE TO RELATED APPLICATION

This application claims priority of U.S. provisional application Ser. No. 60/634,445, filed Dec. 9, 2004.

BACKGROUND OF THE INVENTION

1. Field of the Invention

The invention relates to conjugates of tumor specific antibodies with cytotoxic compounds. The preferred conjugates contain maytansinoid compounds linked to an anti-integrin antibody by a disulfide linkage.

2. Background of the Invention

There have been numerous attempts to improve the efficacy of antineoplastic drugs by conjugating such drugs to monoclonal antibodies (Mabs) against tumor-associated antigens in order to elevate local concentration of the drug by targeted delivery to the tumor. Conversely, the potential for antibodies to actually destroy tumor cells is limited to those antibodies directed to blocking proliferative stimuli, such as the growth factors EGF and Her-2 by blocking the ligand binding to the receptors or blocking signaling to of the receptors (ErbB1 and ErbB2) or those that elicit effector functions (ADCC or CDC). Therefore, a product combining the specificity of a Mab with the killing potential of a metabolic poison has been sought. Examples of the former are doxorubicin conjugated Mab BR96 (Braslawsky, et al. Cancer Immunol Immunother 33:367-374, 1991) and pseudomonas exotoxin fused to anti-growth factor antibodies or fragments (Kreitment, et al., Internat. J. Immunopharm. 14(3):465-72, 1992).

These attempts have encountered unforeseen limitations, such as the requirement for relatively high intracellular concentrations of the toxin compared to the number of external binding sites per cell. If the number of tumor-associated antigens on the cancer cell surface is estimated to be $10^5$ molecules/cell, the cytotoxic agents that can be effectively used in these conjugates must have an $IC_{50}$ value of $10^{-10}$-$10^{11}$ M against target cancer cells. (Chari, R. V. J. Adv. Drug Delivery Rev. 1998, 31, 89-104). Secondly, the drug must either be released upon binding to the target and penetrate the cell or the entire construct must be transported into the cell and toxin cleaved or otherwise activated there.

Some of these drawbacks can be solved to a greater or lesser extent by using a highly potent drug conjugated to an internalizing antibody and using a chemical bond which has enhanced lability under intracellular conditions. Chari et al (Cancer Res. 52:127-131, 1992; Liu et al., Proc. Natl. Acad. Sci USA 93:8618-8623, 1996; U.S. Pat. No. 5,208,020) developed antibody conjugates wherein the antibody is linked to a maytansinoid via a disulfide linkage.

Maytansinoids are plant derived anti-fungal and anti-tumor agents. The isolation of three ansa macrolides from ethanolic extracts of *Maytenus ovatus* and *Maytenus buchananii* was first reported by S. M. Kupchan et al. and is the subject of U.S. Pat. No. 3,896,111 along with demonstration of their anti-leukemic effects in murine models at the microgram/kg dose range. Maytansinoids, however, have unacceptable toxicity, causing both central and peripheral neuropathies, and side effects: particularly nausea, vomiting, diarrhea, elevations of hepatic function tests and, less commonly, weakness and lethargy. Therefore, it has been a focus of research for some time to find the correct targeting moiety along with a suitable chemical process to form a maytansine-antibody conjugate with acceptable half-life of degradation.

In contrast to the high cytotoxicity of free maytansinoid, an antibody conjugate has a toxicity which is several orders of magnitude lower on antigen-negative cells compared to antigen-positive cells. The linkage by disulfide bonding has the advantage that these bonds are readily cleaved inside the target cells by intracellular glutathione, releasing highly toxic free drug. This approach has been applied to antibodies against tumor-associated antigens, for example the C242-DM1 conjugate (Liu et al., Proc. Natl. Acad. Sci USA 93:8618-8623, 1996), and HuN901-DM1 (Chari et al., 2000). However, the application of these conjugates is restricted due to the limited expression of the respective target antigens.

There is, therefore, still the need to improve this approach by using antibodies targeted to the more highly expressed tumor-associated antigens, and optionally, antigens highly expressed during the proliferative and metastatic stages of the malignancy, thus allowing for a natural concentration of toxin to the most virulent cells.

Anti-Integrin Monoclonal Antibodies

Considerable evidence shows that progressive tumor growth is dependent upon angiogenesis, the formation of new blood vessels, to provide tumors with nutrients and oxygen, to carry away waste products and to act as conduits for the metastasis of tumor cells to distant sites (Gastl et al., Oncol. 54:177-184). Recent studies have further defined the roles of integrins in the angiogenic process. During angiogenesis, a number of integrins that are expressed on the surface of activated endothelial cells regulate critical adhesive interactions with a variety of ECM proteins to regulate distinct biological events such as cell migration, proliferation and differentiation. Specifically, the closely related but distinct integrins $\alpha V\beta 3$ and $\alpha V\beta 5$ have been shown to mediate independent pathways in the angiogenic process. An antibody generated against $\alpha V\beta 3$ blocked basic fibroblast growth factor (bFGF) induced angiogenesis, whereas an antibody specific to $\alpha V\beta 5$ inhibited vascular endothelial growth factor (VEGF) induced angiogenesis (Eliceiri, et al., J. Clin. Invest. 103: 1227-1230 (1999); Friedlander et al., Science 270: 1500-1502 (1995)). Therefore, integrins and especially the alpha V subunit containing integrins, are reasonable therapeutic targets for diseases that involve angiogenesis such as disease of the eye and neoplastic disease, tissue remodeling such as restenosis, and proliferation of certain cells types particularly epithelial and squamous cell carcinomas.

Antibody Drug Conjugates

Conjugates of cell binding agents with the highly cytotoxic maytansine has been described (U.S. Pat. Nos. 5,208,020 and 5,416,064; R. V. J. Chari et al., 1992 Cancer Res. 52:127-131). Certain reagents or reactants such as N-hydroxysuccinimidyl esters (NHS) for reaction with protein amine groups have been developed for use in forming drug-protein conjugates. Reagents of this type were generally described by Carlsson et al. (Biochem J. 173: 723, 1978 and in U.S. Pat. No. 4,149,003. Nitro-pyridyl linker reagents for maytansine conjugation to Mabs and other proteins are disclosed in WO2004/016801.

In the above referenced processes, the cell binding agents are modified with a bifunctional agent such as N-Succinimidyl-3-(2-pyridyldithio)propionate (SPDP) to introduce an active disulfide moiety. Reaction with a thiol-containing cytotoxic drug provides a conjugate in which the cell binding agent, such as a monoclonal antibody, and drug are linked via disulfide bonds. It was found that the C-3 hydroxyl position could be modified without loss of activity, in fact, certain esters were found to have enhanced cell killing activity (See Cassady, et al. Chem Pharm Bull 52(1): 1-26, 2004 for a review). U.S. Pat. Nos. 5,208,020 and 5,416,064 specifically teach the use of the activated maytansol ester of N-methyl-N-(3-methyldithiopropanoyl)-L-alanine. The maytansoid moiety from this reaction, and which is released upon reductive cleavage of the disulfide bond, has been designated DM1 [$N^{2'}$-deacetyl-$N^{2'}$-(3-mercapto-1-oxopropyl)-maytansine, CAS Reg. No. 139504-50-0]. Thus, all the conjugates prepared using the methyldithiolated form of DM1 retain an unsubstituted methylene carbon adjacent to the disulfide bond on the drug side of the conjugate (FIG. 1).

In order to enhance the in vivo stability of this disulfide link, it is important to provide sterically hindered disulfide bonds as has been noted previously (Thorpe, et al. Cancer Research 47:5924-31, 1987). This objective can be achieved by using cross-linkers that bear one or two methyl substituents on the carbon atom adjacent to the disulfide bond or using activated drugs bearing at least one substituent on the alpha-carbon atom adjacent the sulfhydryl or disulfide substituent.

While the problems of targeted delivery are now clearly recognized, finding a suitable combination of antibody specificity and affinity, conjugation chemistry, and toxin is unpredictable. It is the object of the present invention to provide novel antibody maytansine conjugates wherein the antibody is directed to cell surface antigens sufficient in number to deliver a cytocidal dose of a maytansinoid and which conjugate has appropriate chemical and biologic stability to provide a therapeutically effective rate of release when administered to a subject.

SUMMARY OF THE INVENTION

It is the object of the present invention to provide novel antibody maytansine conjugates wherein the antibody is directed to cell surface antigens sufficient in number to deliver a cytocidal dose of a maytansinoid and where the antibody is known to be internalized by the cell after binding the target antigen. In a specific embodiment, the conjugates comprise a disulfide bond which has been engineered through substitution of the adjacent methylene carbons to provide a therapeutically effective rate of release when administered to a subject. In a specific embodiment, the invention relates to an antibody-drug conjugate comprising: an antibody that binds to human alphaV integrin subunit conjugated to a cytotoxic agent with an IC50 of $10^{-9}$ M or less, wherein the antibody-drug conjugate exerts a cytotoxic or cytostatic effect on an alpha V integrin expressing cancer cell line. In this embodiment, the antibodies of the invention are specific for at least one alphaV subunit of a heterodimeric integrin receptor, such as an alphaVbeta1, alphaVbeta3, alphaVbeta5, alphaVbeta6, or alphaVbeta8 heterodimeric integrin protein or fragment thereof. The preferred conjugates contain maytansinoid compounds linked to the antibody by a disulfide linkage and the antibody is capable of binding vitronectin and fibrogen.

In one aspect, the antibody conjugates of the invention are represented by the Formula $$[C-L]_m-A \qquad \qquad I$$

where A is a human alphaV integrin subunit specific antibody, wherein said antibody is capable of being internalized by the cell expressing said alphaV subunit; C is a cytotoxin with a $IC_{50}$ of $10^{-9}$ M or less; and L is a linking group which binds the antibody and cytotoxin and further comprises a bond cleavable by components of the intracellular environment; and m represents the average number of cytotoxin molecules linked to the antibody and is an integer from 1-10, specifically from 3-4. The cytotoxin may be selected from the group consisting of maytansinoids, calicheamicins, epothilones, discodermolide, eleuthrobins, dolastatins, cryptophycins, camptothecins, rhizoxin (CAS reg. no. 90996546), or taxane derivatives and such other compounds that exhibit half maximal inhibition (IC50 or GI50) of on tumor cell growth at $10^{-9}$ M or less.

In an aspect of the first object of the invention, the anti-alphaV integrin antibody-maytansinoid conjugate comprises any protein or peptide containing molecule that comprises an antibody that competes for binding to alpha-V subunit of a heterodimeric human integrin receptor with the monoclonal antibody CNTO 95. In one embodiment, the antibody comprises at least a portion of a complementarity determining region (CDR) of a heavy or light chain or a ligand binding portion thereof derived from the antibody designated CNTO 95, in combination with a heavy chain or light chain variable region, a heavy chain or light chain constant region, a framework region, or any portion thereof, that can be incorporated into the antibody with the CDR. The antibody CNTO 95 described herein is a human anti-alphaV antibody derived from immunization of a transgenic mouse containing genes for the expression of human immunoglobulins. Thus, in one embodiment, the invention is directed to antibodies containing at least one CDR region or variable region derived from the CNTO 95 antibody. In a preferred embodiment the antibody is CNTO 95.

In another aspect of the invention, the antibody-maytansinoid conjugate comprises a maytansinol ester which is released upon cleavage of a bond linking the cytotoxin, C, to the linker, L by components of the intracellular environment. In one embodiment, the maytansinoid is esterified at C-3, C-14, C-15, or C-20 with an acylated amino acid where the acyl group bears a protected sulfhydryl group, wherein the carbon atom of the acyl group adjacent the protected sulhydryl group has one or two substituents, said substituents being $CH_3$, $C_2H_5$, linear alkyl or alkenyl having from 1 to 10 carbon atoms, branched or cyclic alkyl or alkenyl having from 3 to 10 carbon atoms, phenyl, substituted phenyl, or heterocyclic aromatic, heterocycloalkyl radical, or H; and wherein the acyl group has a linear chain length of at least two carbon atoms between the carbonyl functionality and the sulfur atom. In a preferred embodiment, the maytansinoid is a 3-maytansinol ester and the acylated amino acid group bears 0, 1 or 2 methyl groups on the carbon atom adjacent to the protected sulhydryl. In a preferred embodiment, the esterified maytansinol is selected from $N^{2'}$-deacetyl-$N^{2'}$-(3-mercapto-1-oxopropyl)-maytansine (DM1, CAS Reg. No. 139504-50-0), $N^{2'}$-deacetyl-$N^{2'}$-(4-mercapto-1-oxopentyl)-maytansine (DM3), and $N^{2'}$-deacetyl-$N^{2'}$-(4-methyl-4-mercapto-1-oxopentyl)-maytansine (DM4).

It is a second object of the invention to provide anti-integrin antibody-maytansinoid conjugate compounds useful for treatment of human proliferative diseases caused by abnormal proliferation and characterized by neovascularization. In a particularly preferred embodiment, the compounds of the invention are used in a method of treating cancer including, breast, colon, rectal, lung, prostate, kidney, liver, pancreatic, esophageal, stomach, endometrial, ovarian, cervical, or bone. The compounds of the invention may be used alone or in combination with other agents in the prevention or therapy of primary cancers or the prevention or therapy of metastatic disease.

In another method of the second object of the invention relates to the combined use of anti-integrin antibody maytansinoid conjugate compounds with chemotherapeutic agents in methods of cancer treatment. The preferred conjugates contain maytansinoid compounds linked to the antibody by a disulfide linkage, and preferred chemotherapeutic agents are doxorubicin, a taxane, a camptothecin, a podophyllotoxin, a nucleoside analog, or a pyrimidine analog.

In a third object of the invention, the antibody-maytansinoid conjugate is prepared in a process whereby the antibody is reacted with a bispecific chemical linker reagent, such as an N-succinimidyl-(2-pyridylthio)alkanoate, and subsequently reacted with a pre-activated maytansinoid whereby disulfide exchange occurs to yield a hindered disulfide linkage between the antibody and the maytansinoid.

In another aspect of the invention the antibody-maytansinoid conjugate is prepared using a maytansinol ester wherein the acyl moiety bears a protected sulfhydryl group.

In one embodiment, the maytansinoid is esterified at C-3, C-14, C-15, or C-20 with an acylated amino acid where the acyl group bears a protected sulfhydryl group, wherein the carbon atom of the acyl group adjacent the protected sulhydryl group has one or two substituents, said substituents being selected from: $CH_3$, $C_2H_5$, linear alkyl or alkenyl having from 1 to 10 carbon atoms, branched or cyclic alkyl or alkenyl having from 3 to 10 carbon atoms, phenyl, substituted phenyl, a heterocyclic aryl moiety, a heterocycloalkyl moiety, or H; and wherein the acyl group has a linear chain length of at least two carbon atoms between the carbonyl functionality and the sulfur atom. In a preferred embodiment, the maytansinoid is a 3-maytansinol ester and the acylated amino acid group bears 0, 1 or 2 methyl groups on the carbon atom adjacent the protected sulhydryl. In a preferred embodiment, the esterified maytansinol is selected from $N^{2'}$-deacetyl-$N^{2'}$-(3-mercapto-1-oxopropyl)-maytansine (DM1, CAS Reg. No. 139504-50-0), $N^{2'}$-deacetyl-$N^{2'}$-(4-mercapto-1-oxopentyl)-maytansine (DM3), and $N^{2'}$-deacetyl-$N^{2'}$-(4-methyl-4-mercapto-1-oxopentyl)-maytansine (DM4).

In a another aspect of the invention, the anti-alphaV integrin antibody-maytansinoid conjugate is prepared by essentially a single step of reacting a maytansinoid bearing a reactive ester with an anti-integrin antibody not previously chemically activated. The reactive ester of the maytansinoid may be a N-succinimidyl, N-sulfosuccinimidyl, N-phthalimidyl, N-sulfophthalimidyl, 2-nitrophenyl, 4-nitrophenyl, 2,4-dinitrophenyl, 3-sulfonyl-4-nitrophenyl or 3-carboxy-4-nitrophenyl ester.

BRIEF DESCRIPTION OF THE DRAWINGS

FIG. 3 is a schematic showing the synthetic method of preparing antibody-maytansinoid conjugates on the invention.

DETAILED DESCRIPTION OF THE INVENTION

1. Definitions

Figure 1:
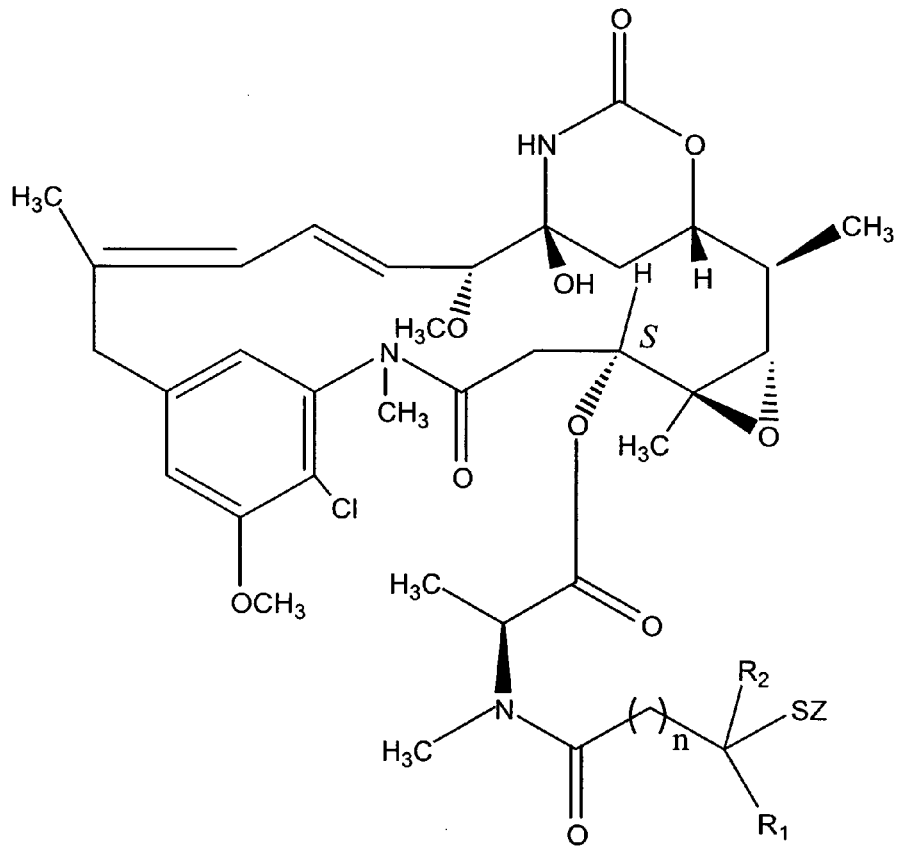
FIG. 1. shows the chemical structure of thiolated maytansine amides with preferred species; DM1, DM3 and DM4 noted.

In order that the present invention may be more readily understood, certain terms are first defined. Additional definitions are set forth throughout the detailed description.

The term "alphaV integrin", "alphaV subunit integrin", and "alphaV subunit containing integrin" are used interchangeably herein to mean alphaV transmembrane glycoprotein subunits of a functional integrin heterodimer and include all of the variants, isoforms and species homologs of alphaV.

Accordingly, antibodies of the invention may, in certain cases, cross-react with alphaV from species other than human, or other proteins which are structurally related to human alphaV (e.g., human alphaV homologs). In other cases, the antibodies may be completely specific for human alphaV and not exhibit species or other types of cross-reactivity.

As used herein, an "antibody" includes whole antibodies and any antigen binding fragment or a single chain thereof. Thus the antibody includes any protein or peptide containing molecule that comprises at least a portion of an immunoglobulin molecule, such as but not limited to at least one complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein, which can be incorporated into an antibody of the present invention. An antibody could be murine, human, humanized, or chimeric.

The "antigen binding fragment" or portion thereof, includes single chain antibodies and fragments thereof. Functional fragments include antigen-binding fragments that bind to a mammalian alpha-V subunit. Examples of binding fragments encompassed within the term "antigen binding portion" of an antibody include (i) a Fab fragment, a monovalent fragment consisting of the VL, VH, CL and CH, domains; (ii) a F(ab')2 fragment, a bivalent fragment comprising two Fab fragments linked by a disulfide bridge at the hinge region; (iii) a Fd fragment consisting of the VH and CH, domains; (iv) a Fv fragment consisting of the VL and VH domains of a single arm of an antibody, (v) a dAb fragment in which the VH and VL domains are expressed on a single polypeptide chain, but using a linker that is too short to allow for pairing between the two domains on the same chain, thereby forcing the domains to pair with complementary domains of another chain and creating two antigen binding sites; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv)). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Such fragments can be produced by enzymatic cleavage, synthetic or recombinant techniques, as known in the art and/or as described herein.

The term "epitope" means a protein determinant capable of specific binding to an antibody. Epitopes usually consist of chemically active surface groupings of molecules such as amino acids or sugar side chains and usually have specific three-dimensional structural characteristics, as well as specific charge characteristics. Conformational and nonconformational epitopes are distinguished in that the binding to the former but not the latter is lost in the presence of denaturing solvents. The term "native conformational epitope" or "native protein epitope" are used interchangeably herein, and include protein epitopes resulting from conformational folding of the integrin molecule which arise when amino acids from differing portions of the linear sequence of the integrin molecule come together in close proximity in 3-dimensional space. Such conformational epitopes are distributed on the extracellular side of the plasma membrane.

The term "human antibody", as used herein, is intended to include antibodies having variable and constant regions derived from or closely matching human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). Thus as used herein, the term "human antibody" refers to an antibody in which substantially every part of the protein (e.g., CDR, framework, $C_L$, $C_H$ domains (e.g., $C_H1$, $C_H2$, $C_H3$), hinge, ($V_L$, $V_H$)) is substantially similar to a human germline antibody. Human antibodies have been classified into groupings based on their amino acid sequence similarities, see e.g. http://people.cryst.bbk.ac.uk/~ubcg07s/. Thus, using a sequence similarity search, an antibody with similar linear sequence can be chosen as a template to create "humanized antibodies".

"Humanization" (also called Reshaping or CDR-grafting) is now a well-established technique for reducing the immunogenicity of monoclonal antibodies (mAbs) from xenogeneic sources (commonly rodent) and for improving the effector functions (ADCC, complement activation, C1q binding). The engineered mAb is engineered using the techniques of molecular biology, however simple CDR-grafting of the rodent complementarity-determining regions (CDRs) into human frameworks often results in loss of binding affinity and/or specificity of the original mAb. In order to humanize an antibody, the design of the humanized antibody includes variations such as conservative amino acid substitutions in residues of the CDRs, and back substitution of residues from the rodent mAb into the human framework regions (backmutations). The positions can be discerned or identified by sequence comparison for structural analysis or by analysis of an homology model of the variable regions' 3D structure. The process of affinity maturation has most recently used phage libraries to vary the amino acids at chosen positions. Similarly, many approaches have been used to choose the most appropriate human frameworks in which to graft the rodent CDRs. As the datasets of known parameters for antibody structures increases, so does the sophistication and refinement of these techniques. Consensus or germline sequences from a single antibody or fragments of the framework sequences within each light or heavy chain variable region from several different human mAbs can be used. Another approach to humanization is to modify only surface residues of the rodent sequence with the most common residues found in human mAbs and has been termed "resurfacing" or "veneering". Known human Ig sequences are disclosed, e.g., www.ncbi.nlm.nih.gov/entrez/query.fcgi; www.ncbi.nih.gov/igblast; www.atcc.org/phage/hdb.htmi; www.kabatdatabase.com/top.html; www.antibodyresource.com/onlinecomp.html; www.appliedbiosystems.com; www.biodesign.com; antibody.bath.ac.uk; http://www.unizh.ch/~antibody/; www.cryst.bbk.ac.uk/~ubcg07s; Kabat et al., Sequences of Proteins of Immunological Interest, U.S. Dept. Health (1983), each entirely incorporated herein by reference.

"Chimeric antibodies" are those antibodies that retain distinct domains, usually the variable domain, from one species and the remainder from another species; e.g. mouse-human chimeras.

The terms "monoclonal antibody" or "monoclonal antibody composition" as used herein refer to a preparation of antibody molecules of single molecular composition. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell. However, generally, the antibody encoding sequences are cloned and inserted into a host cell or a production cell line.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. Recombinant host cells include, for example, CHO lines or a mouse myeloma SP/0 derived cell line.

The term "recombinant human antibody", as used herein, includes all human or humanized antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences.

An "isolated antibody," as used herein, is intended to refer to an antibody which is substantially free of other antibodies having different antigenic specificities (e.g., an isolated antibody that specifically binds to alphaV is substantially free of antibodies that specifically bind antigens other than alphaV). An isolated antibody that specifically binds to an epitope, isoform or variant of human AlphaV may, however, have cross-reactivity to other related antigens, e.g., from other species (e.g., alphaV species homologs). Moreover, an isolated antibody may be substantially free of other cellular material and/or chemicals.

As used herein, "specific binding" refers to antibody binding to a predetermined antigen. Typically, the antibody binds with a dissociation constant ($K_D$) of 10-7 M or less, and binds to the predetermined antigen with a $K_D$ that is at least twofold less than its $K_D$ for binding to a non-specific antigen (e.g., BSA, casein) other than the predetermined antigen or a closely-related antigen.

As used herein, "isotype" refers to the antibody class (e.g., IgM or IgGl) that is encoded by heavy chain constant region genes.

ABBREVIATIONS

| Abs | antibodies, polyclonal or monoclonal |
|---|---|
| aV | integrin subunit alpha V |
| b3 | integrin subunit beta 3 |
| bFGF | basic fibroblast growth factor |
| HUVEC | human umbilical vein endothelial |
| IFN | interferon |
| Ig | immunoglobulin |
| IgG | immunoglobulin G |
| Mab | monoclonal antibody |
| NPB = | N-succinimidyl-5-nitro-(2-pyridyldithio)butyrate |
| SMCC = | succinimidyl 4-(N-maleimidomethyl)cyclohexane-1-carboxylate |
| SMNP = | N-succinimidyl 4-methyl-4-(5-nitro-2-pyridyldithio)pentanoate |
| SMPT = | 4-succinimidyloxycarbonyl-(2-pyridyldithio)toluene |
| SPDB = | N-succinimidyl-4-(2-pyridyldithio)butyrate |
| SPDP = | N-succinimidyl-3-(2-pyridyldithio)propionate |

-continued

| SPP = | N-succinimidyl-4-(2-pyridylthio)pentanoate |
|---|---|
| SP = | N-succinimidyl 4-(2-pyridyl) |
| SS = | sulfosuccinimidyl |
| SSNPP = | sulfosuccinimidyl-N-succinimidyl-4-(5-nitro-2-pyridyldithio)pentanoate |
| VEGF | vascular endothelial growth factor |

2. Compositions

A. Antibody Conjgates of the Invention

The antibody conjugates of the invention are represented by the Formula

$$[C-L]_m-A \qquad \qquad I$$

where A is a human alphaV integrin subunit specific antibody, wherein said antibody is capable of being internalized by the cell expressing said alphaV subunit; C is a cytotoxin with a $IC_{50}$ of $10^{-9}$ M or less; and L is linking group which binds the antibody and cytotoxin and further comprises a bond cleavable by components of the intracellular environment; and m represents the average number of cytotoxin molecules linked to the antibody and is an integer from 1-5, preferably, 3-4. The cytotoxin may be selected from the group consisting of maytansinoids, calicheamicins, epothilones, discodermolide, eleuthrobins, dolastatins, cryptophycins, camptothecins, rhizoxin (CAS reg. no. 90996546), or taxane derivatives and such other compounds that exhibit half maximal inhibition (IC50 or GI50) of on tumor cell growth at $10^{-9}$ M or less.

Linkers comprising intracellularly cleavable bonds include acid-labile linkages such as cis-aconityl linkages, esters, acid-sensistive hydrazone linkages, lysosomally degradable peptide linkers, hydrolase cleavable linkers, peptidase or protease specific linkers, and disulfide (sulphydryl) linkers (see Dyba, M., et al. 2004 Curr Pharm Design 10:2311-2334 for a review). By being capable of more rapid or selective cleavage under intracellular conditions versus the conditions predominating in, for example, the circulation, the linker imparts further specificity and safety to the overall pharmacodynamics of the conjugate. Disulfide linkages are particularly preferred because of the favorable reduction potential within the cellular compartments as well as inducible redox enzyme activation (Saito, G. et al. Adv. Drug Delivery Rev 2003 55:199-215). In one embodiment of the invention, the bond is between a sulfur atom present in the antibody molecule, e.g. in the side chain of a cysteine residue, and another sulfur atom present in the toxic compound. In another embodiment, the linking moiety consists of one or more atoms or chemical groups.

Another major consideration in chemically linking a biologic molecule, such as a recombinant protein, to a chemical compound is that the derivatization chemistry may, and in most cases will, yield a new molecular entity which may have heretofore unknown biologic properties. Thus, it should be understood that the products of physiological cleavage should be designed to yield the intended derivatives with biological activity. The maytansinoids of the invention including DM1, DM3, DM4 and others as shown and described in FIG. 1 retain biological activity.

The anti-alphaV integrin antibody-maytansinoid conjugates of the invention are prepared by chemically linking an anti-alphaV antibody to a maytansinoid molecule without significantly reducing the biological activity of the antibody and providing a maytansinoid, which when released under physiological conditions, retains its cytotoxic potential. Examples of suitable maytansinoids are esters of maytansinol and maytansinol analogues including but not limited to those having a modified aromatic ring and those having modifications at C-19, C-20, or C-14, or C-15, or C-4,5 deoxy. Preferred are maytansinol C-3 esters. Particularly preferred maytansinoids are derivatives of N-methyl-alanine esters of maytansinol ($N^{2'}$-deacetyl-maytansine). Particularly preferred conjugates comprise a disulfide linkage, which when cleaved by reduction, releases a corresponding maytansinoid bearing a free thiol. Thiol containing maytansinoids of the preferred type are shown in FIG. 1: $N^{2'}$-deacetyl-$N^{2'}$-(3-mercapto-1-oxopropyl)-maytansine (DM1, CAS Reg. No. 139504-50-0), $N^{2'}$-deacetyl-$N^{2'}$-(4-mercapto-1-oxopentyl)-maytansine (DM3), and $N^{2'}$-deacetyl-$N^{2'}$-(4-methyl-4-mercapto-1-oxopentyl)-maytansine (DM4).

Conjugates of the antibody molecules of the invention and toxic compound can be formed using any techniques presently known or later developed. For example, the cytotoxic compound can be modified to yield a free amino group and then linked to the antibody molecule via an acid-labile linker, or a photolabile linker. The toxic compound can be condensed with a peptide and subsequently linked to an antibody molecule to produce a peptidase-labile linker. The toxic compound can be treated to yield a primary hydroxyl group, which can be succinylated and linked to an antibody molecule to produce a conjugate that can be cleaved by intracellular esterases to liberate free drug.

In order to create the disulfide linkage between antibody A and the cytotoxin C, preferably, the toxic compound is treated to create a free or protected thiol group, and then one or many disulfide or thiol containing toxic compounds are covalently linked to the antibody molecule via disulfide bond(s). The disulfide bond need not be formed directly with a free thiol of the antibody but can be formed by derivatization of any reactive group within the antibody to introduce a site for disulfide exchange, for example, as by coupling a bifunctional linker to free amine groups in the antibody. For example, antibody molecules can be modified with crosslinking reagents such as N-succinimidyl 3-(2-pyridyldithio)propionate (SPDP), 4-succinimidyl-oxycarbonyl-a-methyl a-(2-pyridyldithio)-toluene (SMPT), N-succinimidyl-3-(2-pyridyldithio)-butyrate (SDPB), N-succinimidyl-4-(2-pyridyldithio) pentanoate (SPP), N-succinimidyl-5-(2-pyridyldithio) pentanoate, 2-iminothiolane (IT), or acetylsuccinic anhydride by known methods.

The anti-alphaV integrin antibody-cytotoxin conjugates of the invention are thus represented by formula II, where maytansinol is esterified at C-3, and the antibody is a anti-alphaV integrin subunit antibody; $R_1$, $R_2$, $X_1$ and $X_2$ are independently H, Me, $C_2H_5$, linear alkyl or alkenyl having from 1 to 10 carbon atoms, branched or cyclic alkyl or alkenyl having from 3 to 10 carbon atoms, phenyl, substituted phenyl, or a heterocyclic aryl moiety, or a heterocycloalkyl moiety; n is 1-5; p is 1-5; and m is 1 to 10.

II

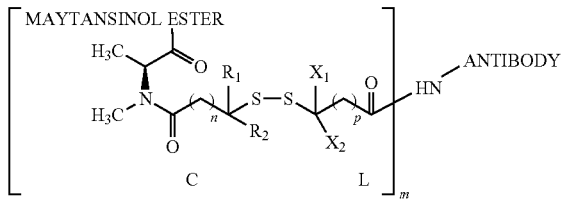

In a preferred embodiment, the linker moiety is a 4-thiopentanoate derived from SPP, or 4-thiopentanoate. The antibody molecule containing free or protected thiol groups thus derived, is then reacted with a disulfide- or thiol-containing toxic compound to produce conjugates. The conjugates can be purified by HPLC or by gel filtration.

B. Anti-Alpha-V Subunit Antibodies of the Invention

In addition to binding AlphaV, the human antibodies or antigen binding fragments or portions thereof as those described above may be selected for their retention of other functional properties of antibodies of the invention, such as:
1) binding to live cells expressing human alphaV;
2) preventing live cell binding to matrix proteins;
3) binding to human alphaV with a KD of $10^{-8}$ M or less (e.g., $10^{-9}$ M or $10^{-10}$ M or less);
4) exhibiting calcium-independent binding to alphaV;
5) binding to a unique epitope on alphaV or belonging to a unique complementation group of antibodies binding to alphaV;
6) inhibition of angiogenesis in vitro or in vivo; or
7) reduction of tumor mass or prevention of tumor growth in vivo.

In another aspect of the invention, the structural features of an human anti-alpha V antibodies of the invention, CNTO 95, are used to create structurally related human anti-Alpha V antibodies that retain at least one functional property of the antibodies of the invention, such as binding to AlphaV. More specifically, one or more CDR regions of CNTO 95 can be combined recombinantly with known human framework regions and CDRs to create additional, recombinantly-engineered, human anti-Alpha V antibodies of the invention.

In a preferred embodiment, the antibody for use in the anti-alphaV antibodies conjugates described herein is a human anti-alpha V antibody derived from immunization of a transgenic mouse containing genes for the expression of human immunoglobulins. Preparation of the antibody is described in detail in PCT publication no. WO 02/12501 and in U.S. Publication No. 2003/040044, both incorporated by reference herein. The antibody includes any protein or peptide containing molecule that comprises at least a portion of a complementarity determining region (CDR) of a heavy or light chain or a ligand binding portion thereof derived from the antibody designated "CNTO 95" (see PCT publication no. WO 02/12501 and U.S. Publication No. 2003/040044), in combination with a heavy chain or light chain variable region, a heavy chain or light chain constant region, a framework region, or any portion thereof, that can be incorporated into an antibody.

Preferably, the CDR1, 2, and/or 3 of the engineered antibodies described above comprise the exact amino acid sequence(s) as those of the fully human Mab designated CNTO 95, Gen0101, CNTO 95, C371A generated by immunization of a transgenic mouse as disclosed herein. However, the ordinarily skilled artisan will appreciate that some deviation from the exact CDR sequences of CNTO 95 may be possible while still retaining the ability of the antibody to bind Alpha V effectively (e.g., conservative substitutions). In a particular embodiment, the antibody or antigen-binding fragment can have an antigen-binding region that comprises at least a portion of at least one heavy chain CDR (i.e., CDR1, CDR2 and/or CDR3) having the amino acid sequence of the corresponding CDRs 1, 2 and/or 3 (e.g., SEQ ID NOS: 1, 2, and/or 3). In another particular embodiment, the antibody or antigen-binding portion or variant can have an antigen-binding region that comprises at least a portion of at least one light chain CDR (i.e., CDR1, CDR2 and/or CDR3) having the amino acid sequence of the corresponding CDRs 1, 2 and/or 3 (e.g., SEQ ID NOS: 4, 5, and/or 6) of the light chain of CNTO95. In a preferred embodiment the three heavy chain CDRs and the three light chain CDRs of the anitbody or antigen-binding fragment have the amino acid sequence of the corresponding CDR of mAb CNTO 95. Accordingly, in another embodiment, the engineered antibody may be composed of one or more CDRs that are, for example, 90%, 95%, 98% or 99.5% identical to one or more CDRs of CNTO 95. Anti-alpha-V subunit antibodies of the present invention can include, but are not limited to, at least one portion, sequence or combination selected from 5 to all of the contiguous amino acids of at least one of SEQ ID NOS:1, 2, 3, 4, 5, 6. An anti-alpha-V subunit antibody can further optionally comprise a polypeptide of at least one of 70-100% of the contiguous amino acids of at least one of SEQ ID NOS: 7, 8. For example, the amino acid sequence of a light chain variable region can be compared with the sequence of SEQ ID NO: 8, or the amino acid sequence of a heavy chain CDR3 can be compared with SEQ ID NO: 7.

As disclosed and claimed herein, the sequences set forth in SEQ ID NOs. 1-8 include "conservative sequence modifications", i.e. amino acid sequence modifications which do not significantly affect or alter the binding characteristics of the antibody encoded by the nucleotide sequence or containing the amino acid sequence. Such conservative sequence modifications include amino acid substitutions, additions and deletions. Modifications can be introduced into SEQ ID NOs: 1-8 or to the nucleic acids encoding them by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in a human anti-Alpha V antibody is preferably replaced with another amino acid residue from the same side chain family.

At least one antibody of the invention binds at least one specified epitope specific to at least one alphaV subunit protein, subunit, fragment, portion or any combination thereof. The at least one epitope can comprise at least one antibody binding region that comprises at least one portion of said protein, which epitope is preferably comprised of at least one extracellular, soluble, hydrophillic, external or cytoplasmic portion of said protein. The at least one specified epitope can comprise any combination of at least one amino acid sequence of at least 1-3 amino acids to the entire specified portion of contiguous amino acids of the SEQ ID NO: 9.

As previously stated, the invention also relates to antibodies, antigen-binding fragments, immunoglobulin chains and CDRs comprising amino acids in a sequence that is substantially the same as an amino acid sequence described herein. Preferably, such antibodies or antigen-binding fragments and antibodies comprising such chains or CDRs can bind human alpha-V subunit with high affinity (e.g., $K_D$ less than or equal to about $10^{-9}$ M). Amino acid sequences that are substantially the same as the sequences described herein include sequences comprising conservative amino acid substitutions, as well as amino acid deletions and/or insertions.

Amino acids in an anti-alpha-V subunit antibody of the present invention that are essential for function can be identified by methods known in the art, such as site-directed mutagenesis or alanine-scanning mutagenesis (e.g., Ausubel, supra, Chapters 8, 15; Cunningham and Wells, Science 244: 1081-1085 (1989)). The latter procedure introduces single alanine mutations at every residue in the molecule. The resulting mutant molecules are then tested for biological activity, such as, but not limited to at least one alpha-V subunit neutralizing activity. Sites that are critical for antibody binding can also be identified by structural analysis such as crystallization, nuclear magnetic resonance or photoaffinity labeling (Smith, et al., J. Mol. Biol. 224:899-904 (1992) and de Vos, et al., Science 255:306-312 (1992)).

3. Methods of Preparation of the Conjugates

The starting compound, maytansinol, as used in the production of compounds DM1, DM3 and DM4 and related activated maytansinoids (FIG. 1) according to this invention can be prepared from maytansine a natural C-3 ester isolated from natural sources (Kupchan et al., J. Amer. Chem. Soc. 97, 5294(1975)) by reductive cleavage. The reagent lithium tri-methoxyaluminum hydride in tetrahydrofuran at −40° C. is particularly useful for this step. Other natural maytansinoid esters may also be advantageously produced by cultivating microorganisms, which belongs to the genus Nocardia (U.S. Pat. No. 4,151,042) or *Actinosynnema* spp. that have been engineered to produce maytansinol, maytanacine or C-3 maytansinol esters such as maytansinol propionate in the culture broth and extracting the compounds from the culture broth for further purification. There are many linking groups known in the art for making antibody maytansinoid conjugates, including, for example disulfide groups, thioether groups, acid labile groups, photolabile groups, peptidase labile peptide linkers, or esters which may be acid labile or esterase cleavable.

As taught in U.S. Pat. No. 5,208,020; esterification of maytansinol or an analogue with the carboxylic acids containing a methyldithio group or other protected thio group, including, for example, N-methyl-N-[3-(methyldithio)-1-oxopropyl]-L-alanine produce the corresponding disulfide-containing maytansinoids. In the case where two diastereomeric products containing the D- and L-acyl side chains result, the diastereomeric maytansinoid esters are readily separated by methods known in the art and the less desirable D-alanyl analog isomer product reduced to recover maytansinol as taught in WO03096782. Reductive cleavage of the disulfide group with dithiothreitol gives the corresponding thiol-containing maytansinoid, which is readily linked via disulfide or thioether linkages to cell binding agents. Thiol-maytansinoids can by purification by HPLC using a C18 column in the reverse phase mode eluting with a gradient of water-acetonitrile.

Figure 2:
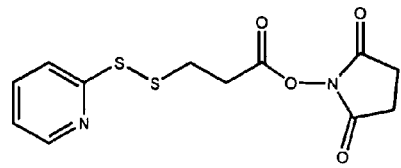
FIG. 2 shows the chemical structures and their chemical acronyms of preferred bifunctional linker reagents of the invention.
Figure 2:
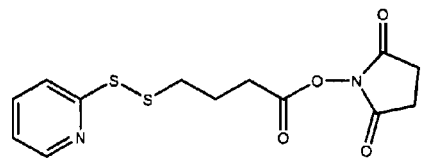
Figure 2:
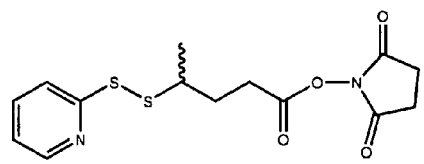
Figure 2:
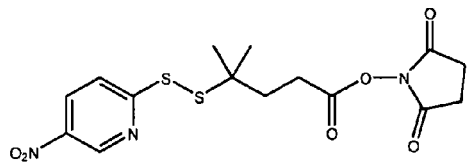
Figure 2:
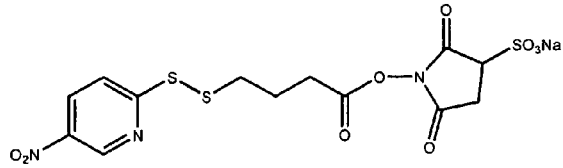
Figure 2:
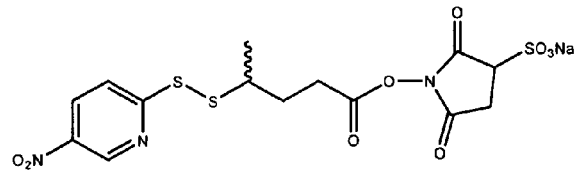
Figure 2:
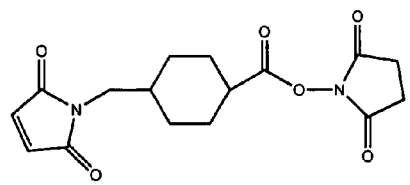

Bifunctional Coupling Reagents. It is known in the preparation of conjugates of two substances, of which at least one comprises a protein or a polypeptide, to use bifunctional agents in order to couple the components of the conjugate covalently, amino groups in the conjugated molecules normally being utilized for the conjugating reaction. Bifunctional protein coupling agents include N-succinimidyl-(2-pyridyldithio)propionate (SPDP), succinimidyl-4-(N-maleimidomethyl)cyclohexane-1-carboxylate, iminothiolane (IT), bifunctional derivatives of imidoesters such as dimethyl adipimidate.HCl, active esters such as disuccinimidyl suberate, aldehydes such as glutaraldehyde, bis-azido compounds suc has bis(p-axidobenzoyl)hexanediamine, bis-diazonium derivatives such as bis-(p-diazoniumbenzoyl)-ethylenediamine), diisocyanates (such as tolyene 2,6-diisocyanate), and bis active fluorine compounds such as 1,5-difluoro-2,4-dinitrobenzene). SPDP is among the most frequently used reagent for this purpose and many other N-succinimidyl-(2-pyridyldithio)-, N-succinimidyl-(5-nitro-2-pyridyldithio)- or N-succinimidyl-(4-pyridyldithio)-short chain alkane acids have proved useful. FIG. 2 shows the structures of commonly used bifunctional linkers and their acronyms.

Conjugation of Activated Antibody to Thiolated Maytansinoid The preparation of CNTO 95-Maytansinoid conjugates followed the method described previously described (Chari et al., Cancer Res. 52: 127-131, 1992 and U.S. Pat. No. 5,208,020) and as outlined in FIG. 3. In this procedure, antibody is modified with bifunctional linker at a ratio of linker to antibody in the range of 5 to 10:1 to introduce dithiopyridyl groups onto the antibody amino acid side chains. The activated antibody is separated from residual linker by G25 gel filtration chromatography. The linker antibody ratio after the purification is less than 5 to 10:1 and typically in the range of 3 to 5:1 and is measured by absorbance at 252 nm and 280 nm. The activated thiol-maytansinoid is added at molar excess to that of the measured linker. Following the conjugation, the mixture is again purified by G25 size exclusion chromatography to yield bulk product.

In the alternative, the anti-integrin antibody maytansinoid conjugate is prepared by essentially a single step of reacting a maytansinoid bearing a reactive ester with anti-integrin antibody not previously chemically activated. The reactive ester of the maytansinoid may be a N-succinimidyl, N-sulfosuccinimidyl, N-phthalimidyl, N-sulfophthalimidyl, 2-nitrophenyl, 4-nitrophenyl, 2,4-dinitrophenyl, 3-sulfonyl-4-nitrophenyl or 3-carboxy-4-nitrophenyl ester. The method is described in publication WO2002098883, the contents of which are incorporated herein by reference.

4. Methods of Using the Conjugates of the Invention

The antibodies of the invention may be administered to a subject in need thereof to prevent, treat, manage or ameliorate a cancer or one or more symptoms thereof. The antibodies of the invention may also be administered in combination with one or more other therapies, preferably therapies useful for the prevention, management or treatment of cancer (including, but not limited to the prophylactic or therapeutic agents listed hereinbelow) to a subject in need thereof to prevent, treat, manage or ameliorate a cancer or one or more symptoms thereof. In a specific embodiment, the invention provides a method of preventing, treating, managing or ameliorating cancer or one or more symptoms thereof, said method comprising administering to a subject in need thereof a dose of a prophylactically or therapeutically effective amount of a formulation comprising the anti-alphaV antibody conjugates of the invention. In another embodiment, the invention provides a method of preventing, treating or ameliorating cancer or one or more symptoms thereof, said method comprising administering to a subject in need thereof a dose of a prophylactically or therapeutically effective amount of anti-alphaV antibody conjugates of the invention in conjunction with a prophylactically or therapeutically effective one or more therapies (e.g., surgery, radiation therapy, or administration of therapeutic agents other than anti-alphaV antibody conjugates). The antibody conjugates of the invention may be used as a first, second, third or fourth line cancer treatment. The invention provides methods for treating or ameliorating one or more symptoms of a cancer in a subject. Further, the invention provides methods for preventing the recurrence of cancer in patients that have been treated and have no disease activity by administering an anti-alphaV antibody conjugate of the invention.

Cancers that can be treated by the methods encompassed by the invention include, but are not limited to, neoplasms, tumors, metastases, or any disease or disorder characterized by uncontrolled cell growth. The cancer may be a primary or metastatic cancer. The cancerous cells may or may not express alphaV subunit integrins. In a preferred embodiment, the cancer that is being managed, treated or ameliorated in accordance with the methods of the invention is a cancer expressing integrin alphaV subunit and has metastasized to the another site or organ within the body of the patient or has the potential to metastasize. Specific examples of cancers that can be treated by the methods encompassed by the invention include, but are not limited to, cancer of the head, neck, eye, mouth, throat, esophagus, chest, bone, lung, colon, rectum, stomach, prostate, breast, ovaries, kidney, liver, pancreas, and brain. Additional cancers include, but are not limited to, the following: leukemias such as but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's lymphoma; myelomas such as multiple myeloma, nonsecretory myeloma, osteosclerotic myeloma, plasma cell leukemia, solitary plasmacytoma and extramedullary plasmacytoma; Waldenstrom's macroglobulinemia; bone cancer and connective tissue sarcomas such as bone sarcoma, myeloma bone disease, osteosarcoma, chondrosarcoma, Ewing's sarcoma, Paget's disease of bone, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as but not limited to, glioma, astrocytoma, nonglial tumor, acoustic neurinoma, craniopharyngioma, medulloblastoma, meningioma, pineocytoma, pineoblastoma, primary brain lymphoma; breast cancer including adenocarcinoma and intraductal carcinoma, and papillary breast cancer; adrenal cancer including pheochromocytoma and adrenocortical carcinoma; thyroid cancer; pancreatic cancer; pituitary cancers; eye cancers not limited to ocular melanoma, choroidal melanoma, cilliary body melanoma, and retinoblastoma; vaginal cancers; vulvar cancer; cervical cancers; uterine cancers not limited to endometrial carcinoma and uterine sarcoma; ovarian cancers; esophageal and other head and neck cancers such as but not limited to, squamous cancer, adenocarcinoma, mucoepidermoid carcinoma, adenosquamous carcinoma, sarcoma, melanoma, plasmacytoma, verrucous carcinoma, and oat cell (small cell) carcinoma; stomach cancers; colon cancers; rectal cancers; liver cancers such as hepatocellular carcinoma and hepatoblastoma, gallbladder cancers; cholangiocarcinomas; lung cancers such as non-small cell lung cancer, squamous cell carcinoma (epidermoid carcinoma), adenocarcinoma, large-cell carcinoma and small-cell lung cancer; testicular cancers, choriocarcinoma (yolk-sac tumor), prostate cancers; penal cancers; oral cancers not limited to squamous cell carcinoma; basal cancers; salivary gland cancers; renal cell cancer and other kidney cancers; and bladder cancers not limited to transitional cell carcinoma (for a review of such disorders, see DeVita, V. T., Hellman, S., & Rosenberg, S. A. Cancer: Principles and practice of oncology. Philadelphia: J. B. Lippincott Company; 6th Edition, 2001). Premalignant conditions may also be treated by the methods and compositions of the invention. Such cancers may include, but not be limited to, follicular lymphomas, carcinomas with p53 mutations, hormone dependent tumors of the breast, prostate and ovary, and precancerous lesions such as familial adenomatous polyposis, and myelodysplastic syndromes.

In a preferred embodiment, the cancer that is being prevented, managed, treated or ameliorated in accordance with the method of the invention is selected from prostate cancer, breast cancer, bone cancer, melanoma, lung cancer and ovarian cancer. In another embodiment, the cancer that is being prevented, managed, treated or ameliorated in accordance with the methods of the invention is selected from metastatic tumors including, but not limited to, tumors that have or may metastasize to the bone (non-limiting examples are prostate, breast and lung cancers that have metastasized or have the potential to metastasize to the bone), tumors that have or may metastasize to the lung, tumors that have or may metastasize to the brain, and tumors that have or may metastasize to other organs or tissues of a subject.

Anti-Cancer Therapies

Any agent or therapy (e.g., chemotherapies, radiation therapies, hormonal therapies, and/or biological therapies or immunotherapies) which is known to be useful, or which has been used or is currently being used for the prevention, treatment, management or amelioration of cancer or one or more symptoms thereof can be used in combination with an anti-alphaV antibody conjugate of the invention in accordance with the invention described herein. Therapeutic or prophylactic agents include, but are not limited to, peptides, polypeptides, proteins, fusion proteins, nucleic acid molecules, small molecules, mimetic agents, synthetic drugs, inorganic molecules, and organic molecules. Examples of the classes of such agents (i.e., anti-cancer agents) include, but are not limited to, cytotoxins, angiogenesis inhibitors, and immunomodulatory agents and agents used to provide relief from pain or to offset the deleterious effects of one or more therapeutic agents (e.g. bisphosphonate use to reduce the hypercalcemic effects of glucocorticoids).

Biologic immunomodulatory agents include: anti-T cell receptor antibodies such as anti-CD3 antibodies (e.g. Nuvion (Protein Design Labs), OKT3 (Johnson & Johnson), or anti-CD20 antibodies Rituxan (IDEC)), anti-CD52 antibodies (e.g. CAMPATH 1H (Ilex)), anti-CD11a antibodies (e.g. Xanelim (Genentech)); anti-cytokine or anti-cytokine receptor antibodies and antagonists such as anti-IL-2 receptor antibodies (Zenapax (Protein Design Labs)), anti-IL-6 receptor antibodies (e.g. MRA (Chugai)), and anti-IL-12 antibodies (CNTO1275 (Centocor)), anti-TNFalpha antibodies (Remicade (Centocor)) or TNF receptor antagonist (Enbrel (Immunex)), anti-IL-6 antibodies (BE8 (Diaclone) and CNTO328 (Centocor)), and antibodies that immunospecifically bind to tumor-associated antigens (e.g., trastuzimab (Genentech).

Angiogenesis inhibitors (i. e., anti-angiogenic agents) include, but are not limited to, angiostatin (plasminogen fragment); antiangiogenic antithrombin III; angiozyme. Bisphosphonates include, but are not limited to, alendronate, clodronate, etidronate, ibandronate, pamidronate, risedronate, tiludronate, and zoledronate.

Specific examples of anti-cancer agents which can be used in accordance with the methods of the invention include, but not limited to: 5-fluoruracil; acivicin; aldesleukin; altretamine; aminoglutethimide; amsacrine; anastrozole; anthramycin; asparaginase; azacitidine; azetepa; azotomycin; batimastat; bicalutamide; bleomycin sulfate; brequinar sodium; bropirimine; busulfan; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; enloplatin; enpromate; epipropidine; epirubicin hydrochloride; erbulozole; esorubicin hydrochloride; estramustine; estramustine phosphate sodium; etanidazole; etoposide; etoposide phosphate; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alpha-2a; interferon alpha-2b; interferon alpha-m; interferon alpha-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; mechlorethamine hydrochloride; megestrol acetate; melengestrol acetate; melphalan; menogaril; mercaptopurine; methotrexate; methotrexate sodium; metoprine; meturedepa; mitomycin; mitosper; mitotane; mitoxantrone hydrochloride; mycophenolic acid; nocodazole; ormaplatin; paclitaxel; pegaspargase; porfromycin; prednimustine; procarbazine hydrochloride; puromycin; rogletimide; safingol hydrochloride; semustine; simtrazene; sparfosate sodium; sparsomycin; spiromustine; spiroplatin; streptonigrin; streptozocin; sulofenur; talisomycin; tegafur; teloxantrone hydrochloride; temoporfin; teniposide; teroxirone; testolactone; thiamiprine; thioguanine; thiotepa; tiazofurin; tirapazamine; topotecan; trimetrexate; trimetrexate glucuronate; triptorelin; uracil mustard; uredepa; vapreotide; verteporfn; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

The invention also encompasses administration of an antibody of the invention in combination with radiation therapy comprising the use of x-rays, gamma rays and other sources of radiation to destroy the cancer cells. In preferred embodiments, the radiation treatment is administered as external beam radiation or teletherapy wherein the radiation is directed from a remote source. In other preferred embodiments, the radiation treatment is administered as internal therapy or brachytherapy wherein a radiaoactive source is placed inside the body close to cancer cells or a tumor mass.

In specific embodiments, patients with breast cancer are administered a prophylactically or therapeutically effective amount of an anti-alphaV antibody conjugate of the invention in combination with the administration of a prophylactically or therapeutically effective amount of one or more other agents useful for breast cancer therapy including but not limited to: doxorubicin, epirubicin, the combination of doxorubicin and cyclophosphamide (AC), the combination of cyclophosphamide, doxorubicin and 5-fluorouracil (CAP), the combination of cyclophosphamide, epirubicin and 5-fluorouracil (CEF), or other agents such as Herceptin, tamoxifen, paclitaxel or taxotere.

In specific embodiments, patients with prostate cancer are administered a prophylactically or therapeutically effective amount of an anti-alphaV antibody conjugate of the invention in combination with the administration of a prophylactically or therapeutically effective amount of one or more other agents useful for prostate cancer therapy including but not limited to external-beam radiation therapy; interstitial implantation of radioisotopes of i.e., rhenium, palladium, or iridium; leuprolide or other LHRH agonists; non-steroidal antiandrogens (flutamide, nilutamide, bicalutamide), steroidal antiandrogens (cyproterone acetate), the combination of leuprolide and flutamide, estrogens such as DES, ethinyl estradiol; low-dose prednisone, or other chemotherapy regimens reported to produce subjective improvement in symptoms and reduction in PSA level.

In specific embodiments, patients with ovarian cancer are administered a prophylactically or therapeutically effective amount of an anti-alphaV antibody conjugate of the invention in combination with a prophylactically or therapeutically effective amount of one or more other agents useful for ovarian cancer therapy including but not limited to: intraperitoneal radiation therapy, such as $^{32}p$ therapy; total abdominal and pelvic radiation therapy, cisplatin, the combination of paclitaxel (Taxol) or docetaxel (Taxotere) and cisplatin or carboplatin, the combination of cyclophosphamide and cisplatin, the combination of cyclophosphamide and carboplatin, the combination of 5-FU and leucovorin, etoposide, liposomal doxorubicin, gemcitabine, ifosfamide, hexamethylmelamine (HMM), or topotecan.

In specific embodiments, patients with tumor metastatic to bone are administered a prophylactically or therapeutically effective amount of an anti-alphaV antibody conjugate of the invention in combination with a prophylactically or therapeutically effective amount of one or more other agents useful for bone metastatic tumor therapy including but not limited to: agents or therapies used in treatment of underlying malignancy such as hornone inhibitors for prostate or breast cancer metastasized to bone, radiotherapy or chemoradiotherapy with bone-seeking radioisotopes of metals (strontium-89 and samarium-153), and bisphosponates (e.g. palmidronate or alendronate).

Cancer therapies and their dosages, routes of administration and recommended usage are known in the art and have been described in such literature as the Physician's Desk Reference (57th ed., 2003) now available through the internet by subscription from PDR® Electronic Library, Thomson Micromedex, Greenwood Village, Colo. (Edition 2004).

Inflammatory Disorder Treatment

The anti-alphaV antibody conjugates of the invention may be administered to a subject in need thereof to prevent, manage, treat or ameliorate an inflammatory disorder or one or more symptoms thereof. The antibodies of the invention may also be administered in combination with one or more other therapies, preferably therapies useful for the prevention, management, treatment or amelioration of an inflammatory disorder (including, but not limited to the prophylactic or therapeutic agents listed in hereinbelow) to a subject in need thereof to prevent, manage, treat or ameliorate an inflammatory disorder or one or more symptoms thereof.

The inflammatory disorders that can be treated by the methods encompassed by the invention include, but are not limited to, asthma, encephilitis, inflammatory bowel disease, chronic obstructive pulmonary disease (COPD), allergic disorders, septic shock, pulmonary fibrosis, undifferentitated spondyloarthropathy, undifferentiated arthropathy, arthritis, osteoarthritis, spondyloarthropathies (e.g. psoriatic arthritis, ankylosing spondylitis, Reiter's Syndrome (reactive arthritis), inflammatory osteolysis, Wilson's disease and chronic inflammation resulting from chronic viral or bacteria infections. In addition, autoimmune disorders are associated with an inflammatory pathology.

Anti-Inflammatory Therapies

The present invention provides methods of preventing, managing, treating or ameliorating an inflammatory disorder or one or more symptoms thereof, said methods comprising administering to a subject in need thereof an anti-alphaV antibody conjugate of the invention and one or more therapies (e.g. prophylactic or therapeutic agents other than antibodies or antibody fragments that immunospecifically bind to alphaV integrins. Any agent or therapy which is known to be useful, or which has been used or is currently being used for the prevention, management, treatment or amelioration of an inflammatory disorder or one or more symptoms thereof can be used in combination with an anti-alphaV antibody conjugate of the invention in accordance with the invention described herein. Examples of such agents include, but are not limited to, immunomodulatory agents, anti-angiogenic agents, anti-inflammatory agents and TNFalpha antagonists.

Specific examples of immunomodulatory agents which can be administered in combination with an anti-alphaV antibody conjugate of the invention to a subject with an inflammatory disorder include, methothrexate, leflunomide, cyclophosphamide, cytoxan, nuran, cyclosporine A, minocycline, azathioprine, antibiotics (e.g. FK506 (tacrolimus)), methylprednisolone (MP), corticosteroids, steroids, mycophenolate mofetil, rapamycin (sirolimus), leflunamide, anti-T cell receptor antibodies (e.g. Orthoclone OKT3 (Johnson & Johnson), Nuvion (Protein Design Labs), or anti-CD20 antibodies (Rituxan (IDEC)), anti-CD52 antibodies (e.g. CAMPATH 1H (Ilex)), anti-IL-2 receptor antibodies (e.g. Zenapax (Protein Design Labs)), anti-IL6 (CNTO 328, Centocor) or anti-IL-6 receptor antibodies (MRA, Chugai), and anti-IL-12 antibodies (CNTO1275, Centocor), anti-IFN antibodies, anti-TNF antibodies, anti-IL-1 antibodies and IL-1alpha/beta antagonists.

Examples of TNFalpha antagonists which can be administered in combination with a anti-alphaV antibody conjugates of the invention to a subject with an inflammatory disorder include proteins, polypeptides, peptides, fusion proteins, antibodies (and antigen-binding fragments thereof) such as antibodies that immunospecifically bind to TNFalpha, nucleic acid molecules (e.g. antisense molecules or triple helices), organic molecules, inorganic molecules, and small molecules that block, reduce, inhibit or neutralizes the function, activity and/or expression of TNFalpha. Examples of TNFalpha antagonists include: infliximab (REMICADE; Centocor), D2E7 (HUMARA; Abbott Laboratories/Knoll Pharmaceuticals Co., Mt. Olive, N.J.), CDP571 which is also known as HUMICADE and CDP-870 (both of Celltech/Pharmacia, Slough, U.K.), TNF-R1 (Amgen), etanercept (ENBREL; Immunex), and inhibitors of other members of the TNFR superfamily of receptors. Other TNF antagonists encompassed by the invention include, but are not limited to, IL-10, which is known to block TNFalpha production and anti-p38 MAPK agents.

Non-limiting examples of anti-inflammatory agents which can be administered in combination with an anti-alphaV antibody conjugate of the invention to a subject with an inflammatory disorder include non-steroidal anti-inflammatory drugs (NSAIDs), steroidal anti-inflammatory drugs, beta-agonists, anticholingeric agents, and methyl xanthines. Examples of NSAIDs include, but are not limited to, aspirin, ibuprofen, celecoxib (CELEBREX), diclofenac (VOLTAREN), etodolac (IODINE), fenoprofen (NALFON), indomethacin (INDOCIN), ketoralac (TORADOL), oxaprozin (DAYPRO), nabumentone (RELAFEN), sulindac (CLINORIL), tolmentin (TOLECTIN), rofecoxib (VIOXX), naproxen (ALEVE, NAPROSYN), ketoprofen (ACTRON) and nabumetone (RELAFEN). Such NSAIDs function by inhibiting a cyclooxgenase enzyme (e.g. COX-1 and/or COX-2). Examples of steroidal anti-inflammatory drugs include, but are not limited to, glucocorticoids, dexamethasone (DECADRON), cortisone, hydrocortisone, prednisone (DELTASONE), prednisolone, and triamcinolone.

In specific embodiments, patients with osteoarthritis are administered a prophylactically or therapeutically effective amount of an anti-alphaV antibody conjugate of the invention in combination with other agents or therapies useful for osteoarthritis prevention, treatment, management or amelioration including but not limited to: analgesics such as acetaminophen, phenacetin; and tramadol, NSAIDs such as aspirin, diflunisal, diclofenac, etodolac, fenamates, fenoprofen, flurbiprofen, ibuprofen, indomethacin, ketoprofen, methylsalicylate, nebumetone, naproxin, oxaprazin, phenylbutazone, piroxicam, sulindac, and tolmetin; cyclooxygenase (Cox)-2-specific inhibitors (CSIs) such as celecoxib and rofecoxib; intra- or periarticular injection of a depot preparations of, for example, glucocorticoids or biopharmaceuticals, and intra-articular injection of hyaluronic acid. The an anti-alphaV antibody conjugate of the invention can also be used in combination with other nonpharmacologic measures in prevention, treatment, management and amelioration of osteoarthritis including but not limited to: irrigation of the osteoarthritic joint, reduction of joint loading; application of heat or cold to the affected joint; capsaicin cream; exercise and other physical therapies, and joint replacement surgery.

In specific embodiments, patients with rheumatoid arthritis are administered a prophylactically or therapeutically effective amount of an anti-alphaV antibody conjugate of the invention in combination with other agents or therapies useful in prevention, treatment, management and amelioration of rheumatoid arthritis include NSAIDs, analgesics, and CSIs as discussed for osteoarthritis. In addition, other therapies may be used concurrently, prior to, or subsequently to administration an anti-alphaV antibody of the invention such as monthly pulses with high-dose glucocorticoids, or intraarticular glucocorticoids; disease-modifying antirheumatic drugs (DMARDs) including methotrexate, gold compounds (e.g. Auranofin), D-penicillamine, the antimalarials (e.g. chloroquine), and sulfasalazine; TNFalpha neutralizing agents such as etanercept and infliximab; immunosuppressive and cytotoxic agents not limited to, azathioprine, leflunomide, cyclosporine, and cyclophosphamide; and surgical interventions such as arthroplasties, total joint replacement, reconstructive hand surgery, open or arthroscopic synovectomy, and early tenosynovectomy of the wrist; external interventions such as a variety of orthotic and assistive devices, and other physical therapies: and dietary supplements such as increasing intake of omega-3 fatty acids (such as eicosapentaenoic acid).

In specific embodiments, patients with chronic obstructive pulmonary disease (COPD) are administered a prophylactically or therapeutically effective amount of an anti-alphaV antibody conjugate of the invention in combination with other agents or therapies useful in prevention, treatment, management and amelioration of COPD including but not limited to: bronchodilators including but not limited to, short- and long-acting beta-adrenergic agonists such as albuterol, pirbuterol, terbutaline, and metaproterenol, oral sustained-release albuterol and inhaled salmeterol; anticholinergics such as ipratropium bromide, and theophylline and its derivatives; glucocorticoids; oxygen; lung transplantation; lung volume reduction surgery; endotracheal intubation, ventilation support; yearly influenza vaccine and pneumococcal vaccination; exercise; and smoking cessation.

In specific embodiments, patients with pulmonary fibrosis are administered a prophylactically or therapeutically effective amount of an anti-alphaV antibody conjugate of the invention in combination with an effective amount of one or more other agents useful for pulmonary fibrosis therapy including but not limited to: oxygen; corticosteroids; cytotoxic drugs (cyclophosphamide or azathioprine); bronchodilators e short- and long-acting beta-adrenergic agonists, anticholinergics, and theophylline and its derivatives); and antihistamines (diphenhydramine and doxylamine).

In specific embodiments, patients with asthma are administered a prophylactically or therapeutically effective amount of an anti-alphaV antibody conjugate of the invention in combination with an effective amount of one or more other agents useful for asthma therapy including but not limited to: adrenergic stimulants (examples include but not limited to, catecholamines, e.g., epinephrine, isoproterenol, and isoetharine; resorcinols, e.g. metaproterenol, terbutaline, and fenoterol; and saligenins, e.g. salbutamol; methylxanthines including theophylline and its various salts; anticholinergics including atropine sulfate, akopine methylnitrate, and ipratropium bromide; glucocorticoids; mast cell stabilizing agents cromolyn sodium and nedocromil sodium; leukotriene modifiers Zileuton, zafirlukast and montelukast; immunosuppressant agents including methotrexate; and acetylcysteine.

In specific embodiments, patients with allergy are administered a prophylactically or therapeutically effective amount of an anti-alphaV antibody conjugate of the invention in combination with an effective amount of one or more other agents useful for allergy therapy including but not limited to: cromolyn; antihistamines; sympathomimetic drugs (both alpha-adrenergic and beta-adrenergic drugs); theophylline and its derivatives; glucocorticoids; and immune desensitization treatments with allergen injections.

Autoimmune Disorder Treatment

The anti-alphaV antibody conjugate of the invention may be administered to a subject in need thereof to prevent, manage, treat or ameliorate an autoimmune disorder or one or more symptoms thereof. The anti-alphaV antibody conjugate of the invention may also be administered in combination with one or more other therapies, preferably therapies useful for the prevention, management or treatment of an autoimmune disorder (including, but not limited to the prophylactic or therapeutic agents listed in hereinbelow) to a subject in need thereof to prevent, manage, treat or ameliorate an autoimmune disorder or one or more symptoms thereof. In a specific embodiment, the invention provides a method of preventing, managing, treating or ameliorating an autoimmune disorder or one or more symptoms thereof, said method comprising administering to a subject in need thereof a dose of a prophylactically or therapeutically effective amount of a liquid formulation of the invention. In another embodiment, the invention provides a method of preventing, managing, treating or ameliorating an autoimmune disorder or one or more symptoms thereof, said method comprising administering to a subject in need thereof a dose of a prophylactically or therapeutically effective amount of a liquid formulation of the invention and a dose of a prophylactically or therapeutically effective amount of one or more therapies (e.g:, prophylactic or therapeutic agents) other than antibodies or antibody fragments that immunospecifically bind to alphaV integrins.

The invention provides methods for managing, treating or ameliorating an autoimmune disorder or one or more symptoms thereof in a subject refractory to conventional therapies for such an autoimmune disorder, said methods comprising administering to said subject a dose of a prophylactically or therapeutically effective amount of the antibodies of the invention. The invention also provides methods for managing, treating or ameliorating an autoimmune disorder or one or more symptoms thereof in a subject refractory to existing single agent therapies for such an autoimmune disorder, said methods comprising administering to said subject a dose of a prophylactically or therapeutically effective amount of an anti-alphaV antibody conjugate of the invention and a dose of a prophylactically or therapeutically effective amount of one or more therapies (e.g. prophylactic or therapeutic agents) other than antibodies or antibody fragments that immunospecifically bind to alphaV integrin. The invention also provides methods for managing, treating or ameliorating an autoimmune disorder or one or more symptoms thereof by administering an anti-alphaV antibody conjugate of the invention in combination with any other treatment to patients who have proven refractory to other treatments but are no longer on these treatments. The invention also provides alternative methods for the management or treatment of an autoimmune disorder where another therapy has proven or may prove too toxic, i.e., results in unacceptable or unbearable side effects, for the subject being treated.

Particularly, the invention provides alternative methods for the management or treatment of an autoimmune disorder where the patient is refractory to other therapies. Further, the invention provides methods for preventing the recurrence of an autoimmune disorder in patients that have been treated and have no disease activity by administering an anti-alphaV antibody conjugate of the invention.

In autoimmune disorders, the immune system triggers an immune response when there are no foreign substances to fight and the body's normally protective immune system causes damage to its own tissues by mistakenly attacking self. There are many different autoimmune disorders which affect the body in different ways. For example, the brain is affected in individuals with multiple sclerosis, the gut is affected in individuals with Crohn's disease, and the synovium, bone and cartilage of various joints are affected in individuals with rheumatoid arthritis. As autoimmune disorders progress, destruction of one or more types of body tissues, abnormal growth of an organ which may be accompanied by neovascularization of said organ or tissue, or changes in organ function may result. The autoimmune disorder may affect only one organ or tissue type or may affect multiple organs and tissues. Organs and tissues commonly affected by autoimmune disorders include red blood cells, blood vessels, connective tissues, endocrine glands (e.g. the thyroid or pancreas), muscles, joints, and skin. Examples of autoimmune disorders that can be treated by the methods of the invention include, but are not limited to, alopecia areata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, fibromyalgia-fbromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, lupus erthematosus, Meniere's disease, mixed connective tissue disease, multiple sclerosis, type 1 or immune-mediated diabetes mellitus, myasthenia gravis, pemphigus vulgaris, pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, Rheumatoid arthritis, sarcoidosis, scleroderma, Sjogren's syndrome, stiff-man syndrome, systemic lupus erythematosus, lupus erythematosus, takayasu arteritis, temporal arteristis/giant cell arteritis, ulcerative colitis, uveitis, vasculitides such as dermatitis herpetiformis vasculitis, vitiligo, and Wegener's granulomatosis.

Autoimmune therapies and their dosages, routes of administration and recommended usage are known in the art and have been described in such literature as the Physician's Desk Refererce (56th ed., 2002 and 57th ed., 2003).

The present invention provides methods of preventing, managing, treating or ameliorating an autoimmune disorder or one or more symptoms thereof, said methods comprising administering to a subject in need thereof an anti-alphaV antibody conjugate of the invention and one or more therapies (e.g., prophylactic or therapeutic agents) other than antibodies or antibody fragments that immunospecifically bind to alphaV integrins. Any agent or therapy which is known to be useful, or which has been used or is currently being used for the prevention, management, treatment or amelioration of an autoimmune disorder or one or more symptoms thereof can be used in combination with an anti-alphaV antibody conjugate of the invention in accordance with the invention described herein. Examples of such agents include, but are not limited to, immunomodulatory agents, anti-inflammatory agents and TNFalpha antagonists. Specifc examples of immunomodulatory agents, anti-inflammatory agents and TNFalpha antagonists which can be used in combination with an anti-alphaV antibody conjugate of the invention for the prevention, management, treatment or amelioration of an autoimmune disorder are disclosed herein above.

In specific embodiments, patients with multiple sclerosis (MS) are administered a prophylactically or therapeutically effective amount of an anti-alphaV antibody conjugate of the invention in combination with other agents or therapies useful in prevention, treatment, management and amelioration of MS including but not limited to: IFN-beta1b (Betaseron) and IFN-alpha2a (Avonex); glatiramer acetate (Copaxone); mitoxantrone; methotrexate; cyclophosphamide; intravenous immunoglobulin; glucocorticoids; methylprednisolone; 2-chlorodeoxyadenosine (cladribine); baclofen (orally or intrathecally via an indwelling catheter); cycloenzaprine hydrochloride; clonazepam; clonidine hydrochloride; carbamazepine; gabapentin; amitriptyline; primidone; ondansetron; isoniazid; oxybutynin; tolterodine; propantheline; bethanecol; terazosin hydrochloride; sildenafil citrate; amantadine; pemoline; high dose vitamins; calcium orotate; gancyclovir; antibiotic; and plasma exchange.

In specific embodiments, patients with psoriasis are administered a prophylactically or therapeutically effective amount of an anti-alphaV antibody conjugate of the invention in combination with other agents or therapies useful in prevention, treatment, management and amelioration of psoriasis including topical steroid-containing preparations; tar (Estar, Psorigel, Fototar cream); topical vitamin D analogues such as calcipotriene ointment; ultraviolet light with or without psoralen; methotrexate; cyclosporine; sulfasalazine; and synthetic retinoids.

In specific embodiments, patients with Crohn's disease are administered a prophylactically or therapeutically effective amount of an anti-alphaV antibody of the invention in combination with other agents or therapies useful in prevention, treatment, management and amelioration of Crohn's disease including but not limited to: antidiarrheals (loperamide, diphenoxylate with atropine, cholestyramine or colestipol); antispasmodics (propantheline, dicyclomine, or hyoscyamine); 5-aminosalicylic acid agents (sulfasalazine, mesalamine (Asacol) and its slow release form (Pentasa); corticosteroids; the immunomodulatory drugs useful in rheumatic diseases—azathioprine, mercaptopurine, cyclosporine, and methotrexate; antibiotics; TNF inhibitors including enteracept and inflixmab; immunosuppressive agents including tacrolimus, mycophenolate mofetil, and thalidomide; nutritional therapies; enteral therapy with elemental diets (e.g., Vivonex for 4 weeks); and total parenteral nutrition.

In specifc embodiments, patients with lupus erythematosus are administered a prophylactically or therapeutically effective amount of an anti-alphaV antibody of the invention in combination with other agents or therapies useful in prevention, treatment, management and amelioration of lupus erythematosus including but not limited to: antimalarials (including but not limited to, hydroxychloroquine); glucocorticoids (e.g., low dose, high dose, or high-dose intravenous pulse therapy can be used); immunosuppressive and immunomodulatory agents including cyclophosphamide, chlorambucil, and azanthioprine, methotrexate and mycophenolate mofetil; androgenic steroids (including but not limited to danazol); and anticoagulants (including but not limited to warfarin).

Non-Malignant or Immunological-Related Cell-Proliferative Diseases

The conjugates of the invention are also useful for treating non-malignant proliferative diseases and, especially those involving angiogenesis. Angiogenesis is know to be a contributing factor in number of pathological conditions in addition to the ability of tumors to grow and metastasize, disorders of the eye including retinopathies, and disorders of the skin including psoriasis and Kaposi's Sarcoma. Representative examples of such non-tumorigenic angiogenesis-dependent diseases include corneal neovascularization, hypertrophic scars and keloids, proliferative diabetic retinopathy, rheumatoid arthritis, arteriovenous malformations (discussed above), atherosclerotic plaques and ischemic heart disease, delayed wound healing, hemophilic joints, nonunion fractures, Osler-Weber syndrome, psoriasis, emphigus vulgaris, Behcet's syndrome, acute respiratory distress syndrome (ARDS), pyogenic granuloma, scleroderma, tracoma, menorrhagia (discussed above) and vascular adhesions.

4. Pharmaceutical Formulations

The invention provides for stable formulations of the anti-alphaV-maytansinoid conjugates, which is preferably an aqueous phosphate buffered saline or mixed salt solution, as well as preserved solutions and formulations containing a preservative as well as multi-use preserved formulations suitable for pharmaceutical or veterinary use, comprising at least one anti-alphaV-maytansinoid conjugate in a pharmaceutically acceptable formulation.

Preferred preservatives include those selected from the group consisting of phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal, or mixtures thereof.

At least one anti-alphaV-maytansinoid conjugate in either the stable or preserved formulations or solutions described herein, can be administered to a patient in accordance with the present invention via a variety of delivery methods including SC or IM injection; transdermal, pulmonary, transmucosal, implant, osmotic pump, cartridge, micro pump, or other means appreciated by the skilled artisan, as well--known in the art.

4. Pharmaceutical Formulations

In a preferred method of administering CNTO 95-maytansinoid, the drug substance is given intravenously from a previously installed catheter equipped with an infusion bag. CNTO 95-mertansine is supplied in 20-ml single-use vials by ImmunoGen, Inc. (Cambridge, Mass.). Each vial contains protein at a concentration of from 0.05 to about 2.0 mg/ml in a buffered solution (pH 6.5±0.5) comprised essentially of monobasic potassium phosphate (0.57 mg/ml), monobasic sodium phosphate monohydrate (0.20 mg/ml), dibasic sodium phosphate (0.555 mg/ml), and sodium chloride (8.16 mg/ml) in purified water, USP. The drug product is prefiltered twice upon instilling the dose volume into the infusion bag by passing it through a low protein-binding 5-μ filter and is administered to patients through an inline 0.22 μm filter within 8 h of preparation. After infusion, the i.v. line should be flushed with fluid to ensure delivery of the full drug dose.

The based on previous experience in human patients with Mab-maytansoid conjugates, given by the intravenous method, doses of ranging from 22 to 295 mg/M$^2$ can be given every three weeks (J Clin Oncol. 21:211-222, 2003).

6. Articles of Manufacture

The invention includes an article of manufacture containing materials useful for the treatment of the disorders described above comprising an anti-alphaV-maytansinoid conjugate, a container and a label or package insert on or associated with the container. The article of manufacture preferably contains at least one vial comprising a solution of at least one anti-alphaV-maytansinoid conjugate with the prescribed buffers and/or preservatives, optionally in an aqueous diluent, wherein said packaging material comprises a label that indicates that such solution can be held over a period of time. The invention may comprise an article of manufacture, comprising packaging material, a first vial comprising lyophilized at least one anti-alphaV-maytansinoid conjugate, and a second vial comprising an aqueous diluent of prescribed buffer or preservative, wherein said packaging material comprises a label that instructs a practioner or patient how to reconstitute the at least one anti-alphaV-maytansinoid conjugate in the aqueous diluent to form a solution.

Suitable containers include, for example, bottles, vials, syringes, etc. The containers may be formed from a variety of materials such as glass or plastic. The container may have a sterile access port (for example the container may be an intravenous solution bag or a vial having a stopper pierceable by a hypodermic injection needle).

At least one active agent in the composition is an anti-alphaV antibody-maytansinoid conjugate. The label or package insert indicates that the composition is used for treating the condition of choice, such as cancer. The package insert herein may indicate that the antibody or composition is used to treat cancer that does not respond, or respond poorly, to treatment with the standard of care as outlined herein for specific diseases and diagnoses. In other embodiments, the package insert may indicate that the antibody-maytansinoid conjugate or composition can be used also to treat metastatic cancer, prostate cancer, breast cancer or colorectal cancer.

While having described the invention in general terms, the embodiments of the invention will be further disclosed in the following examples.

EXAMPLE 1

Production and Characterization of Monoclonal antibody CNTO95

Preparation of the anti-alpha V integrin antibody CNTO95 is described in detail in PCT publication no. WO 02/12501 and in U.S. Publication No. 2003/040044, both incorporated by reference herein. Specifically, the human Mab CNTO 95 was generated by immunizing (CBA/J×C57/BL6/J, GenPharm International) F2 hybrid mice with $\alpha_v\beta_3$ integrin purified from human placenta. The antibody is composed of human variable and IgG1 kappa constant regions. The method of making and the desirable characteristics of CNTO95 have been previously described in WO0212501 and Trikha, et al. 2004, Int. J. Cancer 110 (3): 326-335.

Transgenic mice from GenPharm International express human immunoglobulins but not mouse IgM or Igκ were used. These mice contain human sequence transgenes that undergo V(D)J joining, heavy-chain class switching and somatic mutation to generate a repertoire of human sequence immunoglobulins (Taylor et al., International Immunology 6:579-591 (1993)). The light chain transgene is derived in part from a yeast artificial chromosome clone that includes nearly half of the germline human Vκ region. In addition to several VH genes, the heavy-chain (HC) transgene encodes both human μ and human γ1 (Lonberg et al., Nature 368:856-859 (1994)) and/or γ3 constant regions. A mouse derived from the HC012 genotypic lineage was used in the immunization and fusion process to generate an anti-alphaV monoclonal antibody used in the preparation of a conjugate of the invention.

Human placenta (disrupted using a meat grinder) or M21 human melanoma cells expressing the αVβ3 integrin were extracted with OTG (Octylthioglucoside Pierce) in buffered saline as described (WO0212501). These preparations were emulsified with an equal volume of complete Freund's adjuvant and used to immunize 15 to 17 week old surgically castrated male mouse (GenPharm, Foster City, Calif.) on days 0 and 14 and in incomplete Freunds on days 28, 48, and 56. Three days later splenocytes were harvested from a mouse showing a titer of 1:1280 against alphaVbeta3 using a solid phase EIA format. Fusion was carried out at a 1:1 ratio of murine myeloma cells (SP2/0) to viable spleen cells. Hybridoma supernatants were screened using the EIA microplate assay or EIA capture assay and selected antibody producing lines expanded and retested for the desired properties.

ELISA analysis confirmed that purified antibody from two hybridomas, C371A (also called Mab CNTO 95) and C372A, bind alphaVbeta3 in a concentration-dependent manner. Fifty percent binding is achieved at 0.07 and 0.7 μg/mL for C372A and CNTO 95 respectively. In the same assay, the anti-alphaIIbeta3 antibody, c7E3 IgG, demonstrated fifty-percent maximal binding at 0.07 μg/mL.

To ascertain the unique specificity of CNTO95 competition binding (or complementation) assays were performed using of the following murine antibodies: m7E3 IgG, anti-alphaV-beta3 (clone LM609, Chemicon), anti-alphaVbeta 5 (clone P1F6, Gibco), anti-beta3 (Chemicon, AMAC), or anti-alphaV (clone VNR139, Gibco) antibodies. These results demonstrated that CNTO 95 binds an epitope not shared by the other antibodies tested.

The binding affinity values for purified integrins were compared to binding to receptors expressed on various cell lines using 125-I CNTO 95. A375S2 and M21 cells express both $\alpha_v\beta_3$ and $\alpha_v\beta_5$, HT-29 cells express αvβ5. For comparison, other Mabs capable of binding integrins were used. The Kd was calculated from a saturation binding curve in each case using multiple replicates of multiple lots of antibody. On $\alpha_v\beta_3$ coated plates, the CNTO 95 mean $K_D$ was $2.1\pm1.33\times10^{-10}$ M; and the mean abciximab Kd was $2.5\pm1.46\times10^{-10}$ M. The CNTO 95 mean $K_D$ on $\alpha_v\beta_5$ was $2.5\pm1.04\times10^{-11}$ M. Abciximab showed no binding and no dose-response on $\alpha_v\beta_5$ coated plates.

Figure 4:
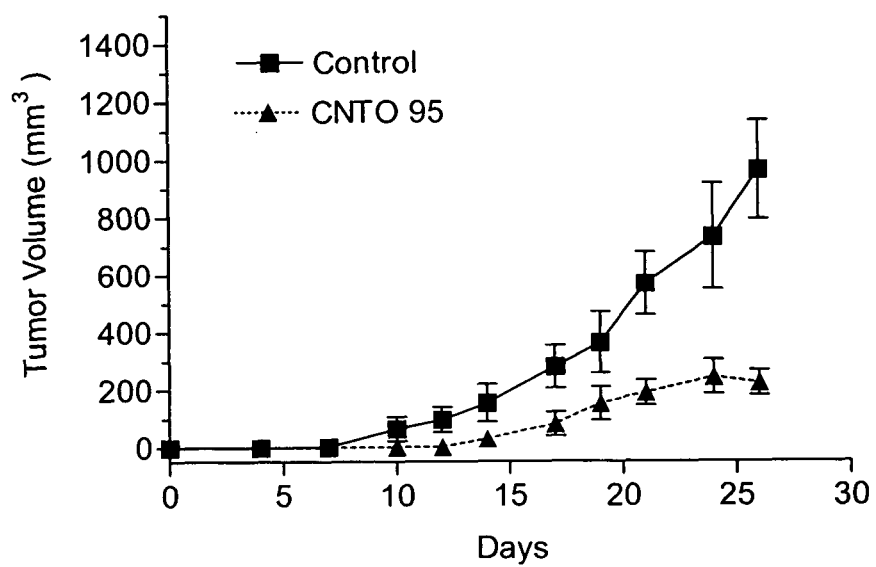
FIG. 4 is a graph showing the change volume over time of a human melanoma tumor in nude mice and the effect of administering CNTO 95. Mice were inoculated subcutaneously with A375.S2 cells ($3 \times 10^6$), and dosing with CNTO 95 or control was initiated three days later. Mice were treated with CNTO 95 or vehicle three times per week at a dose of 10 mg/kg i.p. Each data point is the mean tumor volume from 10 tumor-bearing animals (±SEM). CNTO 95 given three times per week significantly inhibited growth of tumors when compared to control treated animals at day 26 (P=0.0005).

As shown in FIG. 4, dosing with CNTO 95 inhibited growth of human melanoma tumors in nude mice. At day 26, CNTO 95 inhibited tumor growth by approximately 80% compared to tumors from control-treated animals. In this model, CNTO 95 does not interact with host angiogenic vessels since it does not bind mouse integrins, suggesting that blockade of human tumor-expressed integrins alone can inhibit tumor growth in mice independently of antiangiogenic effects For rat studies, female nude rats, aged 6-7 weeks, were purchased from Harlan. Twenty rats were inoculated s.c. with A375.S2 cells ($3\times10^6$) in the flank region (day 1). On day 4, rats were randomly assigned to 2 groups. One group was injected i.v. with CNTO 95 (10 mg/kg in PBS), while the other group received an isotype-matched control IgG (10 mg/kg). Dosing was continued weekly thereafter until day 46 (total of 6 doses). Tumors were measured by calipers twice a week and tumor volumes calculated by the formula (length× width2)/2. Body weights were also recorded weekly.

Figure 5:
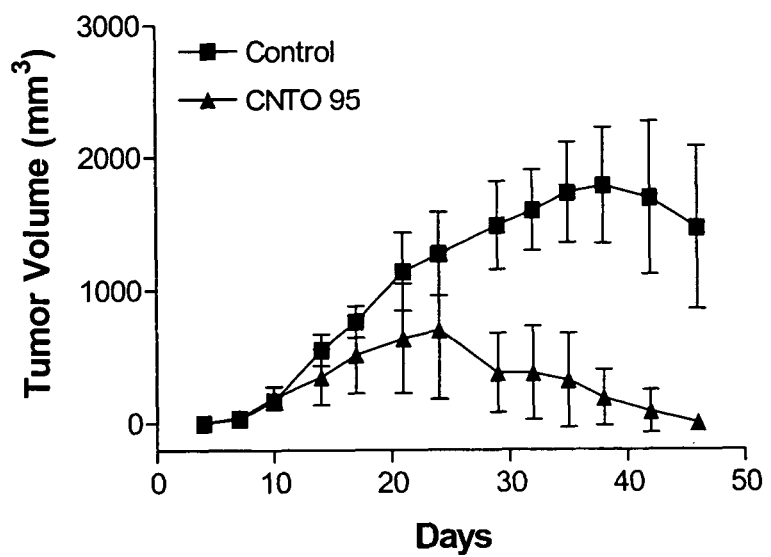
FIG. 5 is a graph showing change volume over time of a human melanoma tumor in nude rats and the effect of administering CNTO 95. Rats were inoculated subcutaneously with A375.S2 cells ($3 \times 10^6$), and therapy with CNTO 95 or control was initiated three days later. Rats were treated with CNTO 95 or vehicle once per week at a dose of 10 mg/kg i.v. Each data point is the mean tumor volume from 9 tumor-bearing animals (±SEM).

In the rat, CNTO 95 is capable of blocking both rat angiogenic integrins and human tumor cell-expressed integrins. Weekly treatment of tumor-bearing nude rats with CNTO 95 at 10 mg/kg reduced tumor growth compared to the isotype-matched human IgG control MAb (FIG. 5). By day 46, treatment with CNTO 95 resulted in significant reduction in final tumor size compared to control-treated nude rats (p=0.0007).

In summary, CNTO 95 is a fully human MAb, which binds members of the alphaV family of integrins with unique specificity, avidity and activity as demonstrated by multiple functional assays showing that it neutralizes the biologic effects of the integrin receptors alphaVbeta3 and alphaVbeta5 in vitro and in vivo. CNTO 95 inhibited adhesion, migration, proliferation and invasion of both tumor and endothelial cells in vitro and demonstrated that binding and blocking multiple alphaV integrin receptors was more effective than blocking of a single integrin alone. In addition, CNTO 95 inhibited angiogenesis and tumor growth in vivo. Growth of human melanoma tumors was significantly reduced by blockage of tumor cell integrins in the mouse model or by combined blockage of tumor cell and host angiogenic integrins in the rat model, highlighting the potential importance of targeting multiple cellular targets for antitumor efficacy.

Results of in vitro models demonstrate that CNTO 95 has potent antiangiogenic properties, inhibiting endothelial cell adhesion, proliferation, migration and capillary sprouting. In addition, CNTO 95 blocked angiogenesis stimulated by both bFGF and M21 melanoma cells in the rat Matrigel model and by bFGF in a primate angiogenesis model. CNTO 95 displayed potent antiangiogenic effects in both a rodent model and a novel nonhuman primate model in cynomulgus monkeys.

In addition to blocking integrins on angiogenic endothelium, the ability to inhibit integrin function on tumor cells themselves reduced the growth of tumors. A number of alphaV integrins have been suggested to play critical roles in tumor cell biology. In a mouse xenograft model where CNTO 95 does not cross-react with host integrins, treatment with CNTO 95 significantly inhibited the growth of v3/5-positive melanoma tumors.

One of the most important features of CNTO 95 is its fully human nature. Because it is fully human, CNTO 95 may be less likely to cause immune responses in patients. Furthermore, because CNTO 95 is able to bind not only alphaVbeta3 and alphaVbeta5 but also other alphaV integrins, such as alphaVbeta 6 and alphaVbeta1, it has the potential to inhibit multiple integrin-mediated events.

EXAMPLE 2

Preparation of CNTO 95-Maytansine Conjugates

Antibody conjugates of thiolated maytansines were prepared for further biological testing starting using bifunctional linkers as described.

CNTO 95 antibody was supplied by Centocor for conjugation. CNTO 95 was supplied at approximately 20 mg/ml (260 mg) total. The antibody was dialysed into Buffer A (50 mM KPi, 50 mM NaCl, 2 mM EDTA pH6.5), then brought to 8 mg/ml in 95% Buffer A, 5% ETOH. The antibody was modified with 6.5 fold molar excess of SPP to introduce the linker for drug conjugation, forming CNTO 95-SS-Py where S-Py is 2-mercaptopyridine. Residual SPP was removed by G25 gel filtration chromatography. The linker to Ab ratio was measured as 4.7. The Ab-SS-Py conjugate was modified with 1.7 fold molar excess of DM1 (MW=737.5 g/mole) to linker, using an antibody concentration of 3.2/mlin 97% Buffer A, 3% dimethylacetamide. Following conjugation, the conjugate was rechromatographed on G25 using PBS, pH 6.5 as the buffer. The resulting conjugate contained 3.2 moles of DM1 per mole of CNTO-95: [Ab]=2.59 mg/ml, [DM1]=38.3 microgm/ml. Calculations were based on absorbance readings at 252 and 280 nm of the filtered material and using extinction coefficients: Ab=224,000 $M^{-1}cm^{-1}$ at 280 nm, DM1=5700 $M^{-1}cm^{-1}$ at 280 nm, Ab=82,880 $M^{-1}cm^{-1}$ at 252 nm and DM1=26,790 $M^{-1}cm^{-1}$ at 252 nm.

The product was analyzed by nonreducing SDS-PAGE, SEC HPLC, and by binding affinity to alphaVbeta3 and alphaVbeta5 protein by ELISA. By PAGE, the product was predominantly a band around 160 kDa with a fainter lower molecular weight band also visible. By SEC HPLC analysis, the fraction of the conjugate eluting a monomer (18.8') was 96% and about 4% of the conjugate eluted as a higher moleculear weight species (16.2'). Binding affintity was calculated by graphing the absorbance v concentration giving an apparent Kd of 3.0 e-11 M for CNTO95 and Kd of 3.5 e-11 M for the conjugate on alphaVbeta5. Both species gave an apparet Kd of approximately 3.0 e-9 on alphaVbeta3.

Figure 3:
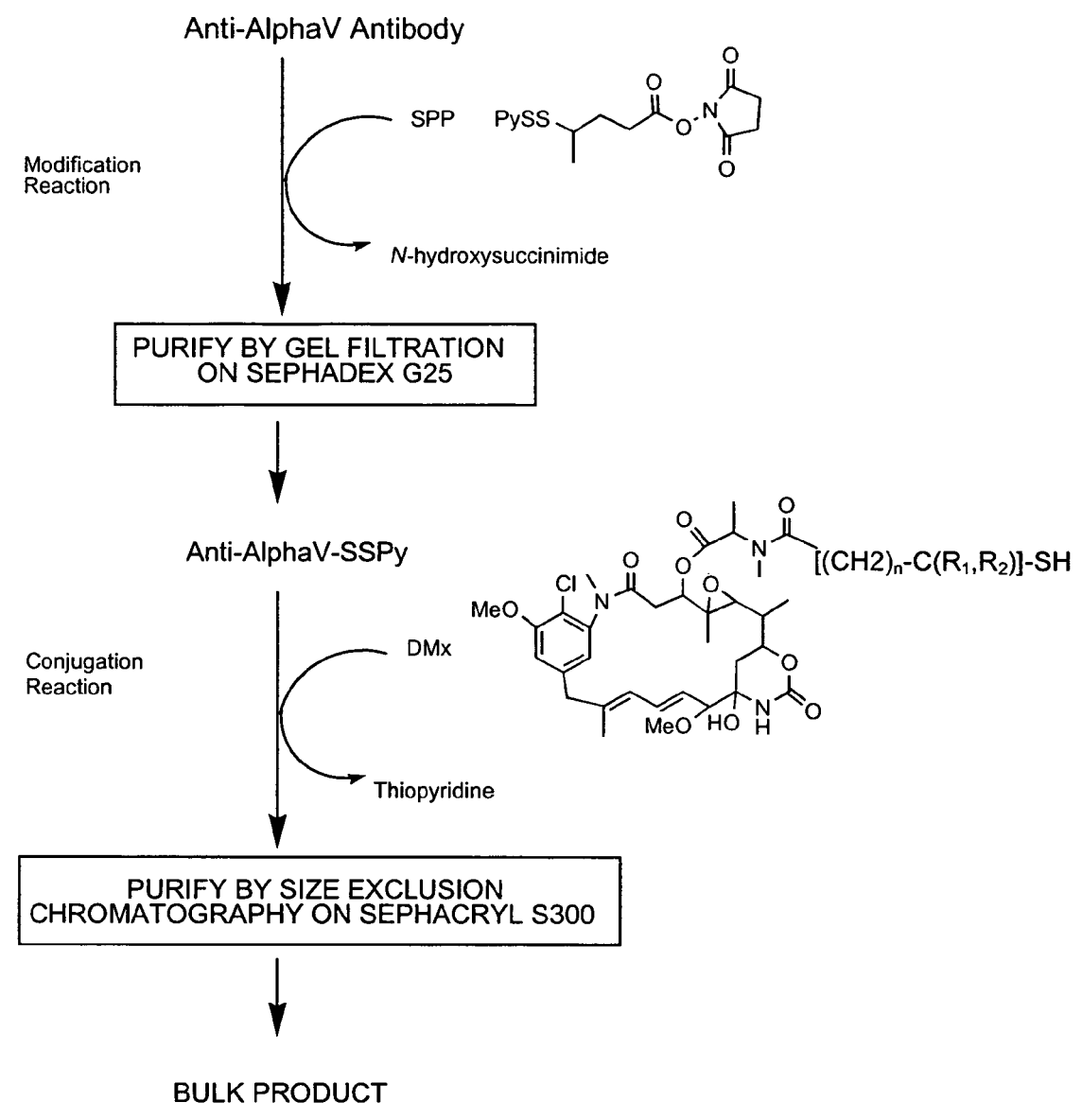

Other batches of CNTO95-SPP-DM1 and CNTO 95 conjugated to DM4 and an irrelevant antibody which targets a non-human antigen, F105, conjugated similarly were prepared in an analogous manner using bifunctional linkers as shown in FIG. 2 and as outlined in FIG. 3. The characterisitics of these preparations are given hereinbelow:

Preparation of CNTO95-SPP-DM1 (CNTO 364). Monoclonal antibody CNTO95 was conjugated to Maytansinoid DM1 with SPP linker as follows: 270.6 mg CNTO95 was conjugated to 3.7 mg of DM1, the resulting 98 ml of conjugate was stored at 2° C. to 8° C. at 2.74 mg/mL in PBS at pH 6.5. The DM1 concentration was determined to 37.6 μg/mL by absorbance. Therefore, the ratio of DM1 per mole of CNTO95 is 2.98 (1 microgrm of DM1 is equivalent to 68.9 microgm of conjugated CNTO95 antibody). By HPLC the preparation was 96.3% monomer with 0.59% free drug.

Preparation of CNTO95-SPP-DM1 (CNTO 364). Monoclonal antibody CNTO95 was conjugated to Maytansinoid DM1 with SPP linker as follows: 104 mg CNTO95 was conjugated to 1.82 mg of DM1, the resulting 26 ml of conjugate was stored at 2° C. to 8° C. at 3.65 mg/mL of conjugated CNTO95-SPP-DM1 antibody in PBS at pH 6.5. The DM1 concentration was determined to 70.07 μg/mL by absorbance. Therefore, the preparation contains a ratio of 3.80 moles of DM1 per mole of CNTO95 (1 μg of DM1 is equivalent to 57.2 μg of conjugated CNTO95 antibody). By HPLC the preparation was 93.4% monomer with 1.61% free drug.

Preparation of CNTO95-SPP-DM1 (CNTO 364). Monoclonal antibody CNTO95 was conjugated to Maytansinoid DM1 with SPP linker as follows: 228 mg CNTO95 conjugated to 4.13 mg of DM1, the resulting 102 ml of conjugate was stored at 2° C. to 8° C. at 2.24 mg/mL of conjugated CNTO95-SPP-DM1 antibody in PBS at pH 6.5. The DM1 concentration was determined to 40.53 μg/mL by absorbance. Therefore, the preparation contains a ratio of 3.93 moles of DM1 per mole of CNTO95 (1 μg of DM1 is equivalent to 55.3 μg of conjugated CNTO95 antibody). By HPLC the preparation was 94.7% monomer with 1.00% free drug.

Preparation of CNTO 95-SSNPB-DM4 (CNTO 365). Monoclonal antibody CNTO 95 was conjugated to Maytansinoid DM4 with SSNPB linker as follows: 121 mg CNTO 95 was conjugated to 2.18 mg of DM4, the resulting 34 ml conjugate was stored at 2° C. to 8° C. at 3.25 mg/mL in PBS at pH 6.5. The DM4 concentration was determined to 64.11 microgm/mL by absorbance. Therefore the ratio of DM4 per mole of antibody is 3.57 (1 microgm of DM4 is equivalent to 55.6 microgm of conjugated CNTO95 antibody). By HPLC the preparation was 95.4% monomer with 3.23% free drug.

Preparation of CNTO95-SSNPP-DM4 (CNTO 366). Monoclonal antibody CNTO 95 was conjugated to Maytansinoid DM4 with SSNPP linker as follows: 101 mg CNTO 95 was conjugated to 1.45 mg of DM4, the resulting 30 ml conjugate was stored at 2° C. to 8° C. at 3.07 mg/mL antibody in PBS at pH 6.5. The DM4 concentration was determined to 48.39 microgm/mL by absorbance. Therefore, the preparation has 2.95 moles of DM4 per mole of CNTO95 (1 μg of DM4 is equivalent to 69.5 μg of conjugated CNTO95 antibody). By HPLC the preparation was 85.9% monomer with 1.18% free drug.

Preparation of CNTO95-SPDB-DM4 (CNTO 365). Monoclonal antibody CNTO 95 was conjugated to Maytansinoid DM4 with SPDB linker as follows: 228.5 mg CNTO95 conjugated to 4.37 mg of DM4, the resulting 104.5 ml conjugate was stored at 2° C. to 8° C. at 2.19 mg/mL of conjugated CNTO95-SPDB-DM4 antibody in PBS at pH 6.5. The DM4 concentration was determined to 41.84 microgm/mL by absorbance. Therefore, the preparation has 3.92 moles of DM4 per mole of CNTO95 (1 μg of DM4 is equivalent to 52.3 μg of conjugated CNTO95 antibody). By HPLC the preparation was 93.6% monomer with 0.55% free drug.

Preparation of CNTO95-SPDB-DM4 (CNTO 365). Monoclonal antibody CNTO 95 was conjugated to Maytansinoid DM4 with SPDB linker as follows: 309 mg CNTO95 conjugated to 5.4 mg of DM4, the resulting 130.7 ml conjugate was stored at 2° C. to 8° C. at mg/mL of conjugated CNTO95-SPDB-DM4 antibody in PBS at pH 6.5. The DM4 concentration was determined to 41.2 microgm/mL by absorbance. Therefore, the preparation has 3.57 moles of DM4 per mole of CNTO95 (1 μg of DM4 is equivalent to 57.5 μg of conjugated CNTO95 antibody). By HPLC the preparation was 93.8% monomer with 0.40% free drug.

Preparation of CNTO95-SPP-DM1 (CNTO 364). Monoclonal antibody CNTO95 was conjugated to Maytansinoid DM1 with SPP linker as follows: 270.6 mg CNTO95 was conjugated to 3.7 mg of DM1, the resulting conjugate was stored at 2° C. to 8° C. at 2.74 mg/mL in PBS at pH 6.5. The DM1 concentration was determined to 37.6 μg/mL by absorbance. Therefore the preparation contains a ratio of 2.98 DM 1 per mole of CNTO95 (1 of DM microgm 1 is equivalent to 68.9 microgm of conjugated CNTO95 antibody). By HPLC the preparation was 96.3% monomer with 0.59% free drug.

Preparation of CNTO95-SPP-DM1 (CNTO 364). Monoclonal antibody CNTO95 was conjugated to Maytansinoid DM1 with SPP linker as follows: 245 mg F105 conjugated to 4.28 mg of DM1, the resulting 91.5 ml conjugate was stored at 2° C. to 8° C. at 2.68 mg/mL of conjugated F105-SPP-DM1 antibody in PBS at pH 6.5. The DM1 concentration was determined to 46.76 microgm/mL by absorbance. Therefore the preparation contains a ratio of 3.79 moles of DM1 per mole of F105 (1 μg of DM1 is equivalent to 57.3 μg of conjugated F105 antibody). By HPLC the preparation was 90.3% monomer with 2.44% free drug.

Preparation of CNTO95-SPP-DM4 (CNTO 366) Monoclonal antibody CNTO95 was conjugated to Maytansinoid DM4 with SPP linker as follows: 76.7 mg CNTO95 conjugated to 1.10 mg of DM4, the resulting 35 ml of conjugate was stored at 2° C. to 8° C. at 2.19 mg/mL of conjugated CNTO95-SPP-DM4 antibody in PBS at pH 6.5. The DM4 concentration was determined to 31.5 microgm/mL by absorbance. Therefore the preparation contains a ratio of 2.96 moles of DM4 per mole of CNTO95 (1 µg of DM4 is equivalent to 69.4 µg of conjugated CNTO95 antibody). By HPLC the preparation was 97.3% monomer with 1.14% free drug.

F105 (1 µg of DM4 is equivalent to 59.4 µg of conjugated F105 antibody). By HPLC the preparation was 85.9% monomer with 3.75% free drug.

Preparation of F105-SPDB-DM4. Monoclonal antibody F105 was conjugated to Maytansinoid DM4 with SPDP linker as follows: 230.5 mg F105 conjugated to 4.12 mg of DM4, the resulting 104.5 ml of conjugate was stored at 2° C. to 8° C. at 2.21 mg/mL in PBS at pH 6.5. The DM4 concentration was determined to 39.41 microgm/mL by absorbance. Therefore, the preparation contains 3.66 moles of DM4 per mole of F105 (1 µg of DM4 is equivalent to 56.0 µg of conjugated F105 antibody). By HPLC the preparation was 89.2% monomer with 0.65% free drug.

In summary, the following species were synthesized for further analysis (Table 6).

TABLE 6

| Compound | Drug | Maytansinol Activating Reagent | Mab Activating Reagent | Methyl Groups Neighboring the Disulfide in the Product (Mab side:Drug side) |
|---|---|---|---|---|
| CNTO364 | DM1 | N-methyl, N-(1-dithiomethyl-3-carboxy-propyl)alanine | SPP or SSNPP | 1:0 |
| CNTO365 | DM4 | N-methyl, N-(1-dithiomethyl-2-methyl-4-carboxy-n-butyl)alanine | SPDB or SSNPB | 0:2 |
| CNTO366 | DM4 | N-methyl, N-(1-dithiomethyl-2-methyl-4-carboxy-n-butyl)alanine | SPP or SSNPP | 1:2 |
| F105-DM1 | DM1 | N-methyl, N-(1-dithiomethyl-3-carboxy-propyl)alanine | SPP or SSNPP | 1:0 |
| F105-DM4 | DM4 | N-methyl, N-(1-dithiomethyl-2-methyl-4-carboxy-n-butyl)alanine | SPDB or SSNPB | 0:2 |
| F105-DM4 | DM4 | N-methyl, N-(1-dithiomethyl-2-methyl-4-carboxy-n-butyl)alanine | SPP or SSNPP | 1:2 |

Preparation of F105-SSNPB-DM4. Monoclonal antibody F105 was conjugated to Maytansinoid DM4 with SSNPB linker as follows: 106 mg F105 was conjugated to 1.84 mg of DM4, the resulting 25 ml conjugate was stored at 2° C. to 8° C. at 3.85 mg/mL in PBS at pH 6.5. The DM4 concentration was determined to 73.45 µg/mL by absorbance. Therefore, the ratio of DM4 per mole of antibody is 3.57 (1 microgm of DM4 is equivalent to 57.5 microgm of conjugated F105 antibody). By HPLC the preparation was 85.1% monomer with 1.92% free drug.

Preparation of F105-SSNPB-DM4. Monoclonal antibody F105 was conjugated to Maytansinoid DM4 with SSNPB linker as follows: 106 mg F105 was conjugated to 1.84 mg of DM4, the resulting 30 ml conjugate was stored at 2° C. to 8° C. at 3.46 mg/mL in PBS at pH 6.5. The DM4 concentration was determined to 57.93 µg/mL by absorbance. Therefore the ratio of DM4 per mole of antibody is 3.32 (1 microgm of DM1 is equivalent to 65.4 microgm of conjugated F105 antibody). By HPLC the preparation was 88.8% monomer with 1.85% free drug.

Preparation of F105-SSNPP-DM4. Monoclonal antibody F105 was conjugated to Maytansinoid DM4 with SSNPP linker as follows: 105 mg F105 conjugated to 1.76 mg of DM4, the resulting 28 ml of conjugate was stored at 2° C. to 8° C. at 3.41 mg/mL in PBS at pH 6.5. The DM4 concentration was determined to 62.87 µg/mL by absorbance. Therefore, the preparation contains 3.45 moles of DM4 per mole of

EXAMPLE 3

CNTO 95-Maytansine Conjugate Binding to Tumor Cells

The ability and affinity of CNTO95-Maytansinoid conjugate binding to living cells was tested.

Materials and Methods. CNTO 95, Centocor lot #95-VF30AO3-1, 20 mg/ml in PBS; CNTO 364 (CNTO 95-SPP-DM1), ImmunoGen lot #1806-164, 37.6 mg/ml of DM1, 2.74 mg/ml of conjugated antibody, Endotoxin level <0.1 EU/mg; CNTO 365 (CNTO 95-SPDB-DM4), ImmunoGen lot #2020-78, 41.2 mg/ml of DM4, 2.36 mg/ml of conjugated antibody, Endotoxin level <0.1 EU/mg; CNTO 366 (CNTO95-SPP-DM4), ImmunoGen lot #2020-48, 31.5 mg/ml of DM4, 2.19 mg/ml of conjugated antibody, Endotoxin level <0.1 EU/mg.

Cells: HT29 human colon carcinoma and A549 human lung carcinoma cells were from ATCC and maintained in alphaMEM supplemented with 10% fetal bovine serum (FBS). A2780 human ovarian carcinoma cells were obtained from National Cancer Institute. A2780 cells were cultured in RPMI 1640 medium containing 10% FBS. Cells were harvested, rinsed, suspended in serum free DMEM, and sequentially incubated for 60 minutes on ice with serial diluted CNTO 95, CNTO 364, CNTO 365 and CNTO 366 and FITC-labeled anti-human antibody (10 mg/ml). Absence of primary antibody or substitution of primary antibody with isotype matched antibody served as negative controls. Cells were immediately analyzed with a FACS Scan II flow cytometer (Becton Dickinson, Mountain View, Calif.). Data was analyzed with GraphPad Prism software using non-liner regression to determine the concentration at 50% maximal binding (Table 7). The effective binding constant was changed less than two-fold in most cases.

TABLE 7

| Compound | EC50 (mg/ml) | | |
|---|---|---|---|
| | HT29 | A549 | A2780 |
| CNTO 95 | 0.14 | 0.18 | 0.17 |
| CNTO 364 | 0.19 | 0.27 | 0.27 |
| CNTO 365 | 0.21 | 0.34 | 0.27 |
| CNTO 366 | 0.29 | 0.42 | 0.30 |

EXAMPLE 4

Cytoxicity of CNTO 95-Maytansine Conjugates to Tumor Cells

The ability of CNTO95-Maytansinoid conjugates to kill tumor cells over time was tested in vitro.

CNTO 364 (CNTO 95-SPP-DM1), ImmunoGen lot #1806-164, 37.6 µg/ml of DM1, 2.74 mg/ml of conjugated antibody, Endotoxin level <0.1 EU/mg. CNTO 365 (CNTO 95-SPDB-DM4), ImmunoGen lot #2020-78, 41.2 µg/ml of DM4, 2.36 mg/ml of conjugated antibody, Endotoxin level <0.1 EU/mg. CNTO 366 (CNTO95-SPP-DM4), ImmunoGen lot #2020-48, 31.5 µg/ml of DM4, 2.19 mg/ml of conjugated antibody, Endotoxin level <0.1 EU/mg.

Human HT29 human colon carcinoma and human non-small cell lung carcinoma cells A549 (ATCC) were cultured in αMEM supplemented with 10% FBS at 37° C. in the presence of 5% $CO_2$. Cells were seeded into white 96-well tissue culture plates (5000 cells/well) in culture medium and incubated for 16 hrs. Serial dilutions of immunoconjugates were added to each appropraite wells (0-20 µg/ml). Tissue culture plates were incubated at 37° C. for 96 hrs. ATPLIte assay was performed acording manufacturer's instruction. Data was analyzed with GraphPad Prism software using non-liner regression (Table 8) to determine the concentration at half maximal cell number as measured by luminosity.

TABLE 8

| Immunoconjugate | EC50 (µg/ml) | |
|---|---|---|
| | HT29 | A549 |
| CNTO 364 | 1.0 | 1.2 |
| CNTO 365 | 0.24 | 0.3 |
| CNTO 366 | 1.0 | 1.5 |

EXAMPLE 5

CNTO 95-DM1 Treatment of Rats Bearing Human Melanoma-Derived Tumors

The efficacy of CNTO 364 compared to CNTO95 against advanced s.c. A375.S2 human melanoma cells was investigated. CNTO 95-DM1 was prepared by ImmunoGen, Inc. Lot #1716-74B, stock concentration: 2.59 mg/ml. 5 mg/kg of CNTO 95-DM1 is equivalent to 74 µg/kg of DM1. CNTO 95 was from Centocor, Lot #5380-027, stock concentration=20 mg/ml. Human IgG-DM1: ChromPure human IgG was from Jackson ImmunoResearch Laboratories. Human IgG-DM1 was prepared by ImmunoGen, Lot #1762-50, stock concentration 2.8 mg/ml. 5 mg/kg of this conjugate is equivalent to 76 µg/kg of DM1. Maytansine: ImmunoGen, Lot #1710-121, stock concentration=16.38 µg/ml in PBS, pH 6.5. The stock solution of Maytansine was diluted with PBS to 15 and 7.5 µg/ml. PBS: ImmunoGen, pH 6.5. A375.S2 human melanoma cells were purchased from ATCC and subpassaged and stored in frozen aliquots at Centocor Cell Biology Services.

Figure 6:
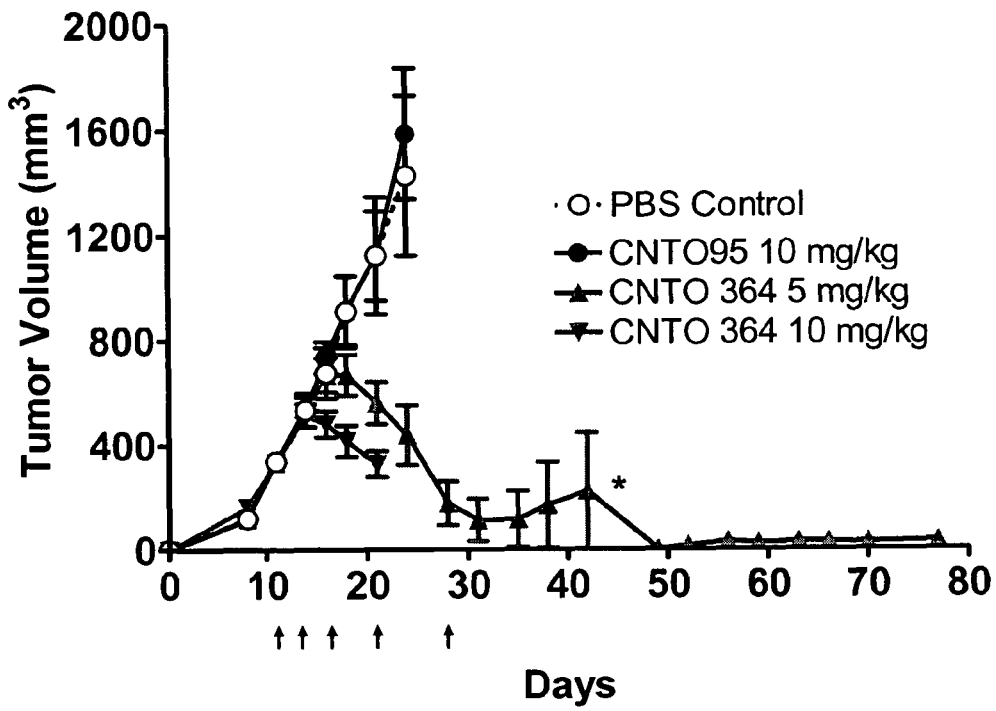
FIG. 6 is a graph showing the growth of A375.S2 human melanoma cells over time in nude mice. Tumor volumes are expressed as mean+/−SEM (n=9 or 10). The arrows indicate intravenous drug injections. The asterisk indicates that one non-responding animal was sacrificed since its tumor volume was over 1500 mm3.

Nine-week-old athymic nude rats were subcutaneously inoculated with A375.S2 human melanoma cells. On day 14, when average tumor volumes reached to 250-300 $mm^3$, animals were randomized to groups of 9/10 and treatment initiated. CNTO 95-DM1 and appropriate control compounds were intravenously injected (three injection every other day in the first week followed by one injection per week for two weeks on days 11, 14, 16, 21 & 28. Tumor sizes and body weights were recorded. FIG. 6 shows the change in tumor volumes over time for human melanoma in nude mice. Tumor volumes are expressed as mean+/−SEM (n=9 or 10). The arrows indicate intravenous drug injections. The asterisk that one non-responding animal was sacrificed since its tumor volume was over 1500 $mm^3$. All animals were sacrificed on day 35. Tumor volumes were expressed as mean+/−SEM (n=9 or 10). The arrows indicate intravenous drug administration. CNTO95-DM1 at 5 mg/kg blocked tumor growth and reduced the average tumor volume whereas CNTO95 at 10 mg/kg had no effect in this experiment.

Figure 7:
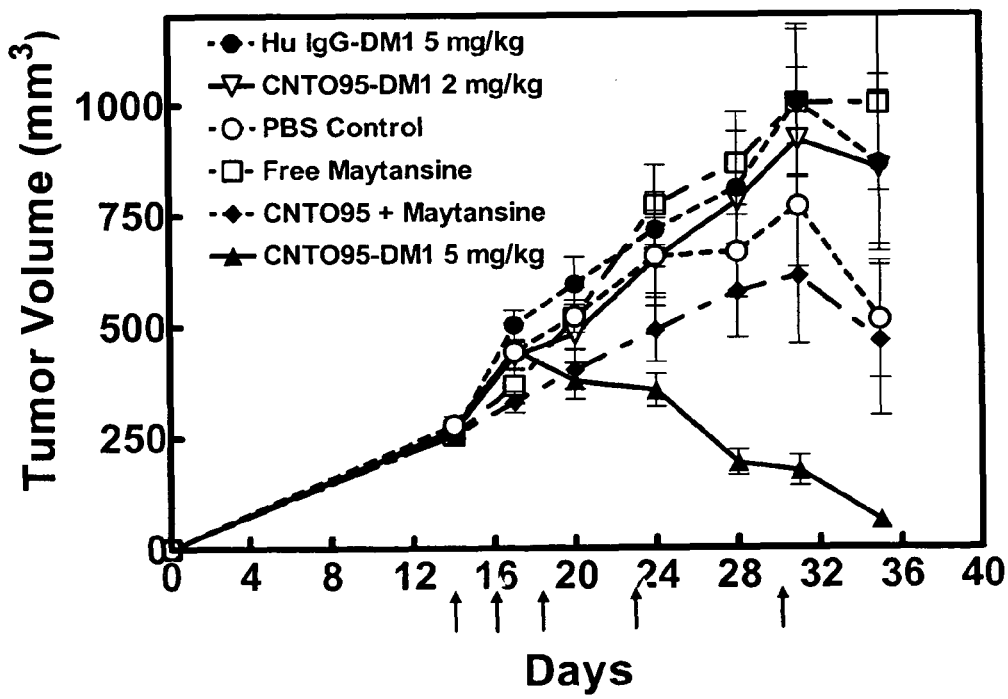
FIG. 7 is a graph showing the growth of human A375.S2 melanoma cells in athymic nude rats. On day 14, when the average tumor volumes reached 250 mm$^3$, the animals were randomly grouped and the first dose was administered. All animals were sacrificed on day 35. Tumor volumes were expressed as mean+/−SEM (n=9 or 10). The arrows indicate the days of intravenous drug administration.

In a second experiment in rats, the average tumor volumes reached to 250 $mm^3$ on day 14. Animals were randomly grouped and the first dosing was intravenously administered on day 14. Subsequent injections were given on D 16 and 18 of the same week and then once per week thereafter on D 23 and D 31. All animals were sacrificed on day 35. CNTO 95-DM1 5 mg/kg caused complete regression of A375.S2 human melanoma xenografts in female athymic rats (FIG. 7). Control compounds including PBS, free CNTO 95, irrelevant antibody-DM1 conjugate, free maytansine, and free CNTO 95 plus free maytansine did not show any significant effects.

EXAMPLE 6

CNTO 95-DM1 Treatment of Rats Bearing Human Colon Carcinoma-Derived Tumors

The efficacy of CNTO 364 compared to CNTO95 against advanced s.c. HT29 human colon carcinoma was investigated.

CNTO 364, ImmunoGen lot #1806-50, protein concentration 2.53 mg/ml, concentration of DM1 41.8 mg/ml, ratio of DM1 to CNTO 95 3.6 mole of DM1 per mole of CNTO 95. PBS or antibody F105-DM1 were used as controls F105-DM1; ImmunoGen lot #1806-44, protein concentration 2.2 mg/ml, concentration of DM1 38.3 mg/ml, ratio of DM1 to F105 3.8 mole of DM1 per mole of F105. All test articles have been tested for endotoxin contamination and LAL values are below 1.0 EU/mg. The HT29 human colon carcinoma cell line, which expresses avb3, avb5, and avb6 integrins, was obtained from Centocor's cell bank. This cell line was determined to be free from mycoplasma and bacterial agents. Cells were cultured in aMEM supplemented with 10% FBS, 1% pyruvate, and 1% MEM non-essential amino acid in the presence of 5% CO2 at 37° C.

Seventy female athymic rats obtained from Harlan Laboratories (Indianapolis, Ind.) were used in this study. Rats were injected with $5 \times 10^6$ HT29 cells subcutaneously (0.2 ml of 25×10⁶ cells/ml) on the rear flank area (dorsal side, approximately 0.5 inches caudal to the last rib and 0.5 inches from the backbone). All rats were monitored daily (work days) for the appearance of palpable tumor. The animals were stratified by individual tumor volume into seven groups, each containing 9 animals (Table 9). The mean starting tumor volume for all groups was between 250-260 mm3.

TABLE 9

| Group | N | CNTO 364 (mg/kg) | Days of Dosing |
|---|---|---|---|
| 1) PBS | 9 | 0 | 7, 14, 21, 28, and 35 |
| 2) F105-DM1 | 9 | 25 | 7 and 14 |
| 3) CNTO 364 | 9 | 3 | 7, 14, 21, 28, and 35 |
| 4) CNTO 364 | 9 | 6 | 7, 14, 21, 28, and 35 |
| 5) CNTO 364 | 9 | 10 | 7, 14, 21, 28, and 35 |
| 6) CNTO 364 | 9 | 15 | 7, 14, and 35 |
| 7) CNTO 364 | 9 | 25 | 7 and 14 |

On the day of grouping (Day 0), animals were weighed and intravenously injected with control antibody F105-DM1 at 25 mg/kg or CNTO 364 at 3, 6, 10, 15 or 25 mg/kg. All test and control articles were given in a volume of 1 ml/100 gm of body weight. CNTO 364 at 3, 6, and 10 mg/kg groups was administered i.v. on a q7dx5 schedule. CNTO 364 at 15 mg/kg was dosed on day 7, 14, and 35. CNTO 364 at 25 mg/kg and F105-DM1 at 25 mg/kg was dosed on days 7 and day 14. The latter two groups were euthanized because of significant body weight loss (more than 10% from day 0) in accordance with the facility's IACUC guidelines (FIG. 8).

Tumor volume measurements were recorded twice weekly. Tumors were measured with calipers in two dimensions (length and width) in millimeters (mm). Tumor volume (mm3) was calculated using the formula V=(length×width×width)/2. Statistics were performed with GraphPad Prism software using unpaired t-test.

Figure 9:
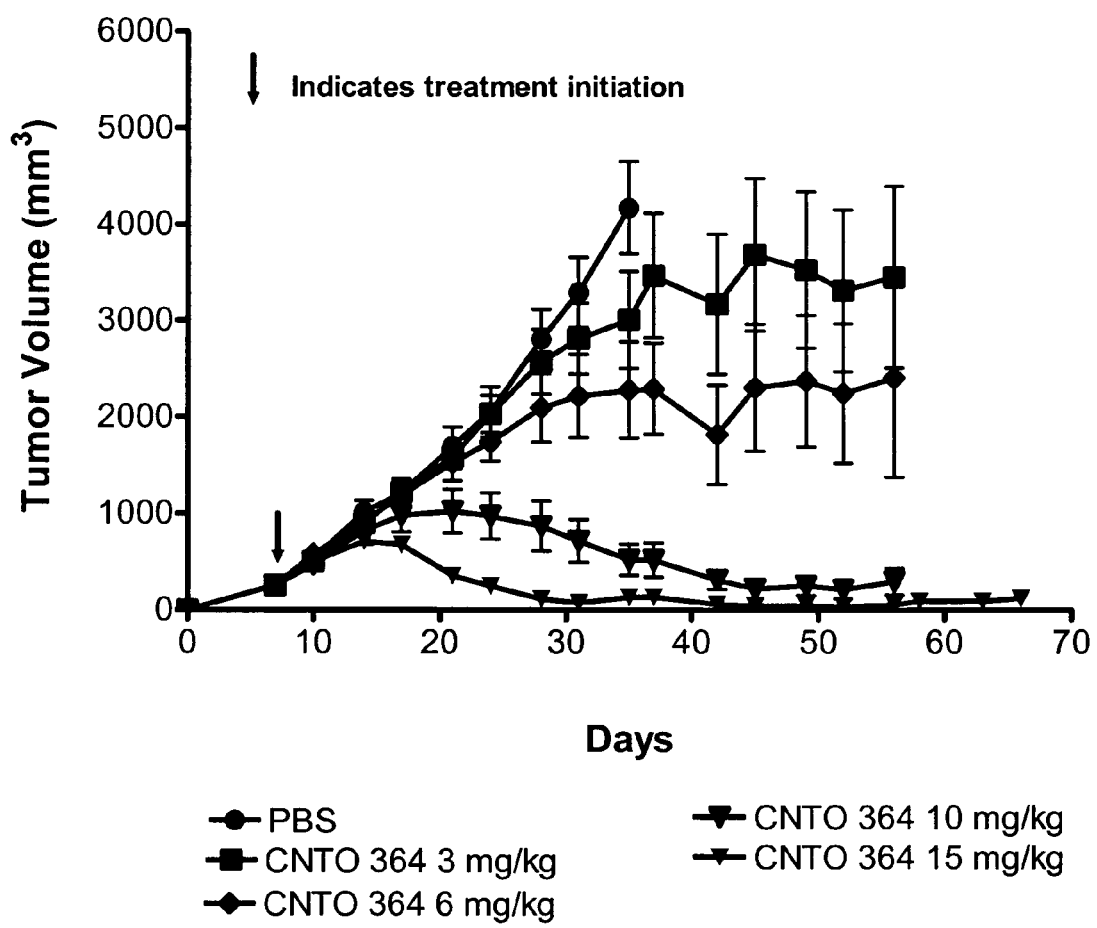
FIG. 9 is a graph showing the change in tumor volume over time in the same animals as in FIG. 8.
Figure 10:
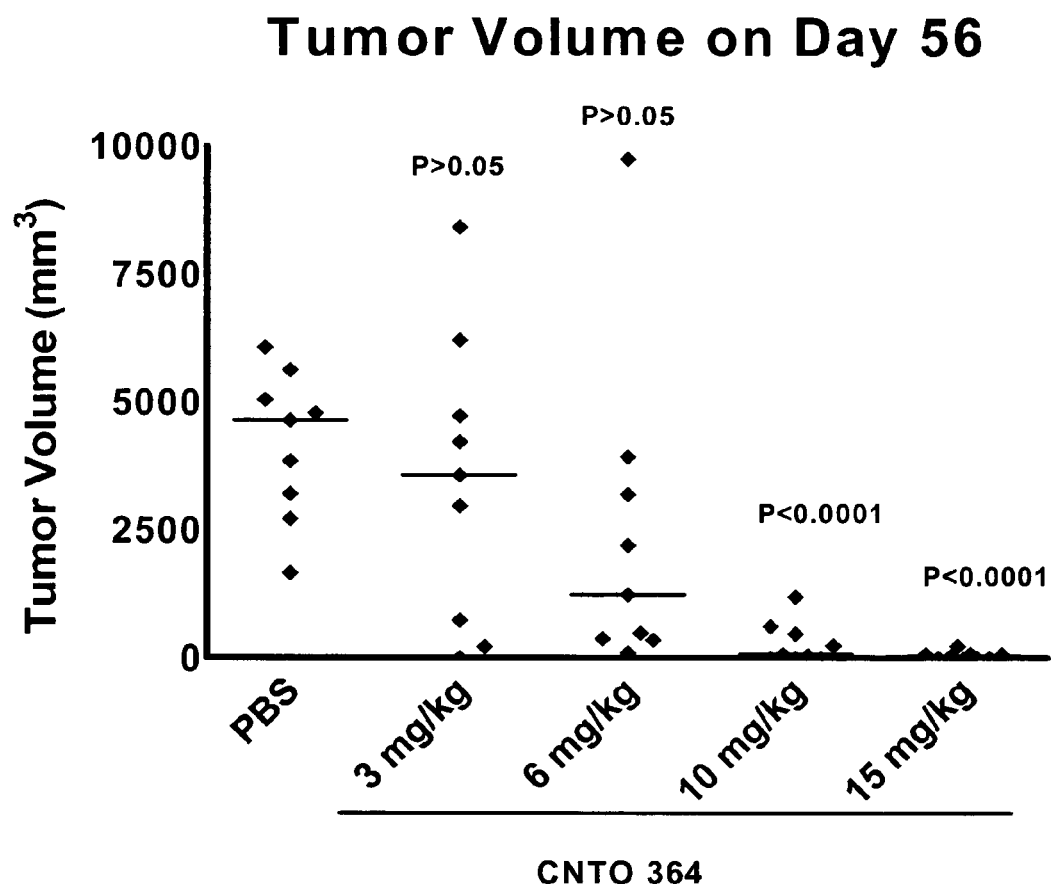
FIG. 10 is a graph showing the individual tumor volumes for all of the animals in the groups as described in FIG. 8.

CNTO 364 inhibited the growth of established colon tumors in a dose-dependent manner (FIG. 9). CNTO 364 at 10 mg/kg on q7dx5 dosing schedule produced 3 complete tumor regressions and 2 partial regressions out of 9 animals (FIG. 10). Treatment with CNTO 364 at 15 mg/kg on day 7, 14 and 35 produced 4 complete regressions and 4 partial regressions in the 9 tumor bearing animals. The PBS control group was terminated on 35 post tumor cell implantation (mean tumor volume over 5000 mm3). At that time the difference in tumor volumes between the CNTO 364 at 10 mg/kg and 15 mg/kg treated groups versus PBS control had a P value of <0.0001 using a two-tailed unpaired t test.

Figure 8:
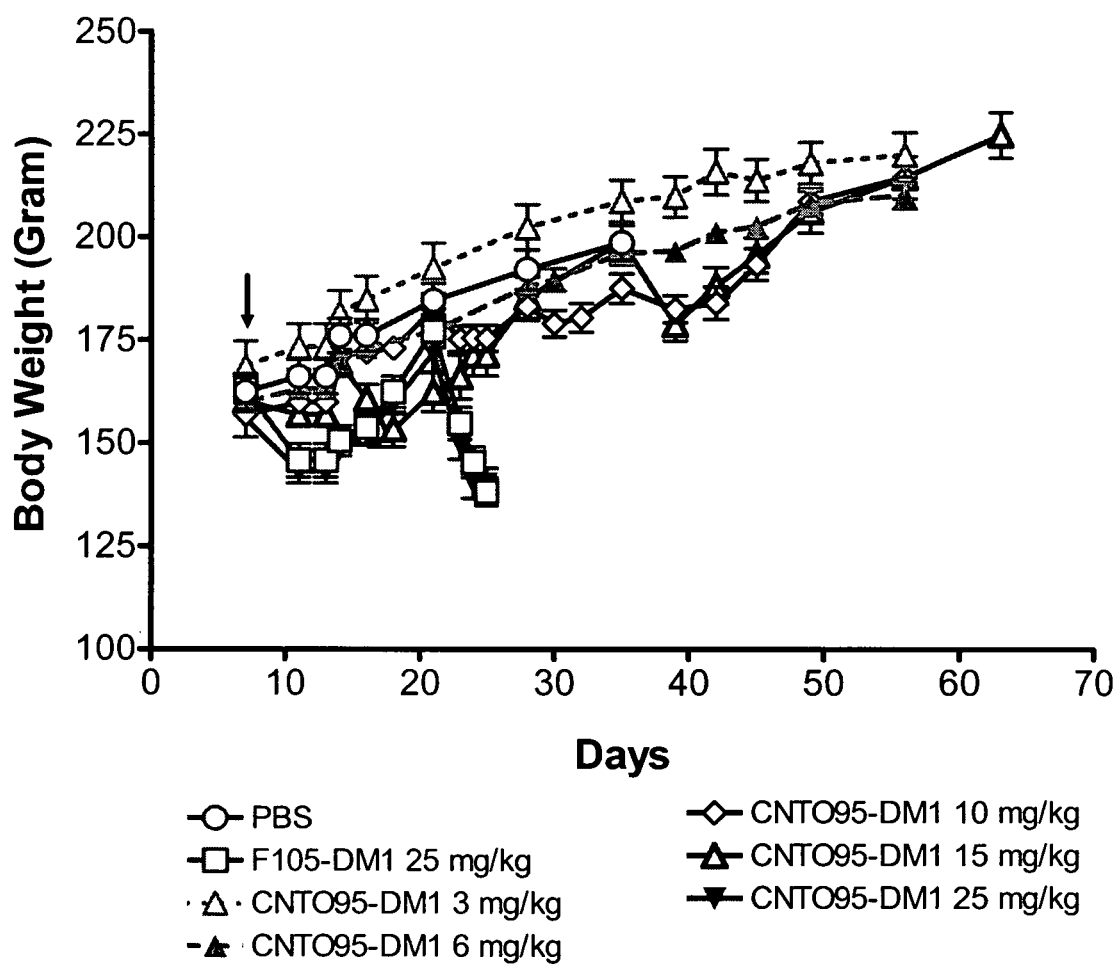
FIG. 8 is a graph showing the changing total body weight over time in tumor bearing mice injected on day 7 after tumor implantation and again every 7 days X5 with 3, 6, or 10 mg/kg CNTO 364; on day 7 and 14 for 25 mg/kg CNTO364 or F105-DM1, and on day 7, 14 and 35 with 15 mg/kg CNTO364.

Two consecutive injections for both CNTO 364 at 25 mg/kg and F105-DM1 at 25 mg/kg were toxic and produced unacceptable body weight loss (FIG. 8). However, a single injection of CNTO 364 at 25 mg/kg completely regressed advanced HT29 human colon carcinoma tumors with mean tumor volume of above 4000 mm3 (not shown)

EXAMPLE 7

CNTO 95-DM1 Treatment of Rats Bearing Human Lung Carcinoma-Derived Tumors

This study was conducted to evaluate the in vivo efficacy of a CNTO 95-DM1 conjugate, in female athymic rats bearing A549 human lung carcinoma. The CNTO 95 was prepared at Centocor, (Malvern, Pa.) and the conjugation of DM1 performed by ImmunoGen (Cambridge, Mass.). CNTO 364 is (CNTO95-SPP-DM1) was as described in Example 1.

Human lung carcinoma cell line A549 (ATCC) were cultured in MEMalpha containing 10% FBS and cells were prepared in serum free αMEM for subcutaneous implantation in athymic rats. The rear flank region of female athymic rats (6 weeks of age Harlan Laboratory, Indianapolis, Ind.) were implanted with 5×10⁶ cells subcutaneously (0.2 ml of 25×10⁶ cells/ml) on the rear flank area (dorsal side, approximately 0.5 inches caudal to the last rib and 0.5 inches from the backbone). When mean tumor volumes reached to 250 mm³, animals were stratified into dosage groups with similar average tumor volumes (Table 10) and dosed intravenously on days 17 and 29 after tumor cell injection.

TABLE 10

| Group | Drug | Dose on Day 17 and 29 |
|---|---|---|
| 1 | PBS | N/A |
| 2 | F105-DM1 | 15 mg/kg |
| 3 | CNTO 364 | 15 mg/kg |
| 4 | CNTO 95 alone | 15 mg/kg |
| 5 | CNTO 95 + Maytansine | 15 mg/kg + 260 microgm/kg |
| 6 | Maytansine alone | 260 microgm/kg |

Figure 11:
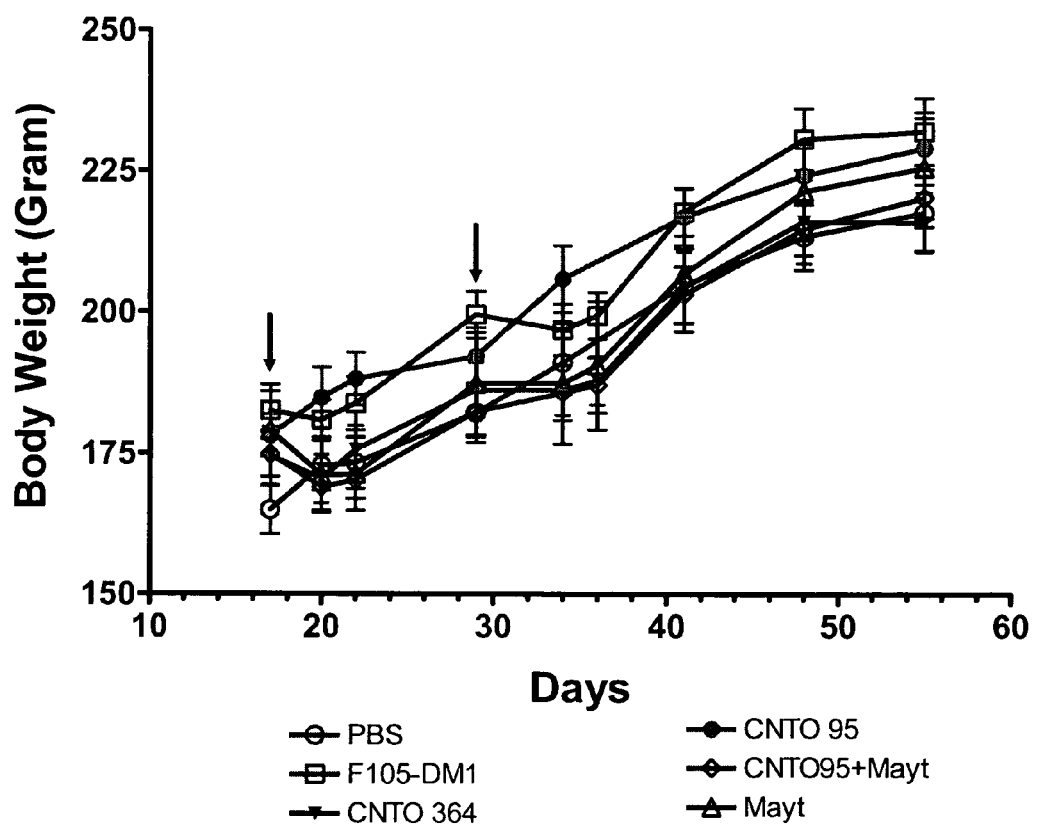
FIG. 11 is a graph of mean body weight+/−SEM (n=6) over time for nude rats bearing subcutaneous human A549 human lung carcinoma tumors and treated with CNTO 364 at 15 mg/kg or with control treatments. The arrows indicate the times of intravenous drug injections.

Tumor volume measurements were recorded twice weekly. Tumors were measured with electronic Vernier calipers in two dimensions (length and width) in millimeters (mm). Tumor volume (mm³) was calculated using the formula V=(length×width×width)/2. Tumor volumes are expressed as mean+/−SEM (n=6). These results were plotted over time, FIG. 12, where the arrows indicate the time of intravenous drug injections. Using body weight as a indicator for tolerability (FIG. 11) also shows that the CNTO 364 dosing schedule used in this study as well tolerated by animals, producing only a 3% body weight transient loss in initial body weight after the first dosing.

Figure 12:
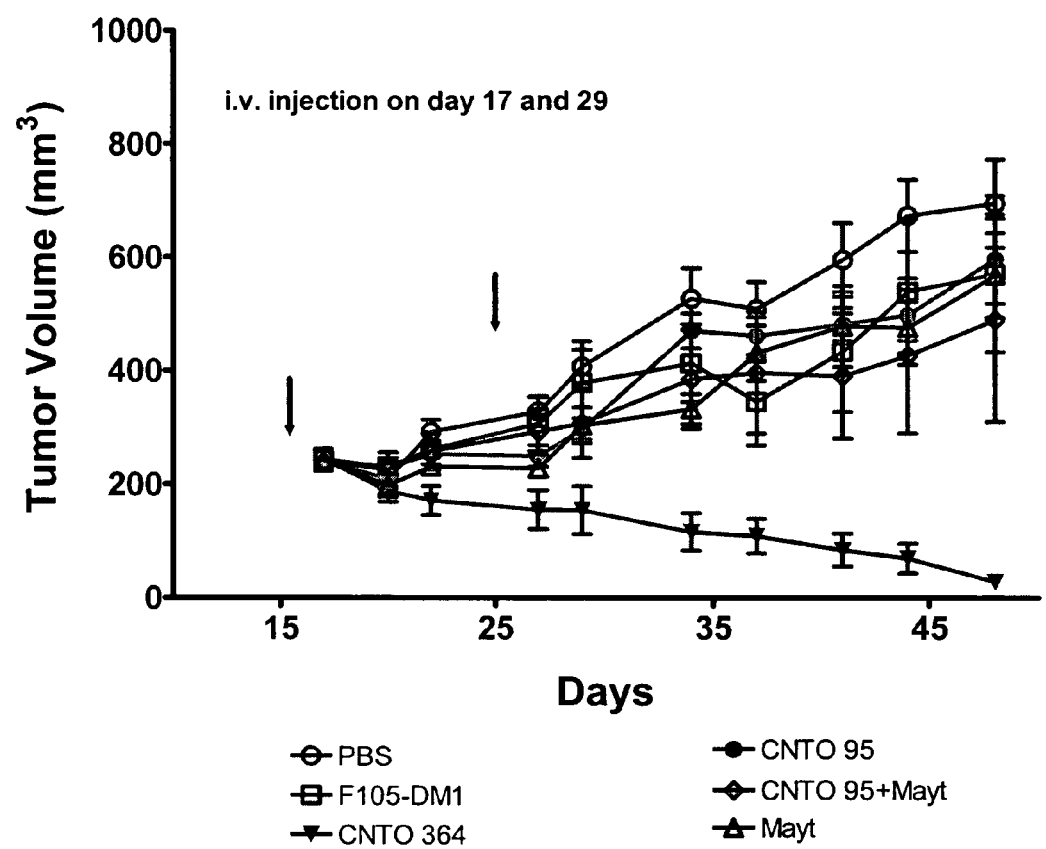
FIG. 12 is a graph showing the growth of human A549 human lung carcinoma tumors in female athymic rats. CNTO 364 (15 mg/kg) treatment regressed established A549 human lung carcinoma tumors in female athymic rats.
Figure 13:
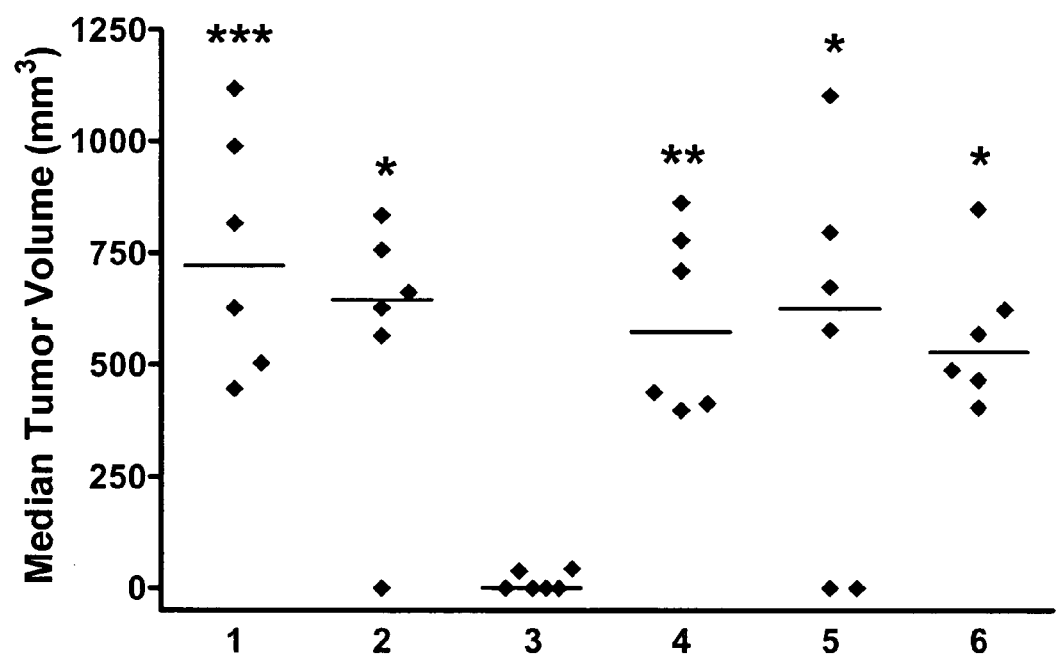
FIG. 13 is a scatter plot showing individual tumor weights at the termination of the study of growth of human A549 human lung carcinoma tumors in female athymic rats treated with 15 mg/kg CNTO364 or control substances. The horizontal lines indicate the median of each study group.

One-way analysis of variance (ANOVA) with Bonferroni test was performed with GraphPad Prism 4 software (GraphPad Software, Inc., San Diego, Calif.) using a 95% confidence interval. Referring to FIG. 12: Group 1, PBS; group 2, F105-DM1 at 15 mg/kg; group 3, CNTO 364 at 15 mg/kg; group 4, CNTO 95 alone at 15 mg/kg; group 5, CNTO 95 at 15 mg/kg plus maytansine at 260 mg/kg; group 6, maytansine alone at 260 mg/kg. P value was determined by one-way analysis of variance (ANOVA) with the Bonferroni test for multiple comparisons. *P>0.05, CNTO 364 v.s. F105-DM1, CNTO 95 plus maytansine or maytansine alone; P<0.01, CNTO 364 v.s. CNTO 95 alone; *P<0.001, CNTO 364 v.s. PBS Conjugation of DM1 to CNTO 95, a large molecule, might change the pharmcokinetic properties of DM1 by prolonging the half-life of DM1 in vivo. To exclude this possibility, an irrelevant antibody F105-DM1 immunoconjugate was included in this study to determine if the activity of CNTO 95-DM1 conjugate was CNTO 95-dependent. Since CNTO 95 is an anti-angiogenic and anti-tumor compound and DM1 is a cytotoxic agent, it is possible that the anti-tumor activity was due to the simple additive effects of free CNTO 95 and free DM1. Therefore, free CNTO 95, free CNTO 95 plus free maytansine, and free maytansine dosed groups were included as controls. As shown in FIG. 13, CNTO 364 at 15 mg/kg eliminated six out of six tumors A549 lung tumor xenograft on the qx12dx2 dosing schedule. One complete tumor regression in the F105-DM1 group and two in the CNTO 95 plus maytansine group were observed. These results demonstrate the superiority of the CNTO 95-DM1 immunoconjugate, CNTO 364, in A549 lung tumor regression. Animals treated with CNTO364 on this dosing regimen showed a transient skin toxicity and body weight loss, no overt signs of severe toxicity.

EXAMPLE 8

Comparison of Conjugate Structures in a Human Colon Carcinoma Tumor Models

An advanced tumor model using subcutaneously implanted HT29 human colon tumor-derived cells in immunocompromised rats was chosen to examine tolerability and potency of various linkages used to prepare immunoconjugates of CNTO 95.

CNTO 95-SPP-DM1 (CNTO 364), CNTO 95-SSNPB-DM4 (CNTO 365), CNTO 95-SSNPP-DM4 (CNTO 366), and the Mab F105 equivalents of these were prepared by ImmunoGen (Cambridge, Mass.). One hundred female athymic rats (4-6 weeks of age) were obtained from Harlan Laboratories.

Figure 14A:
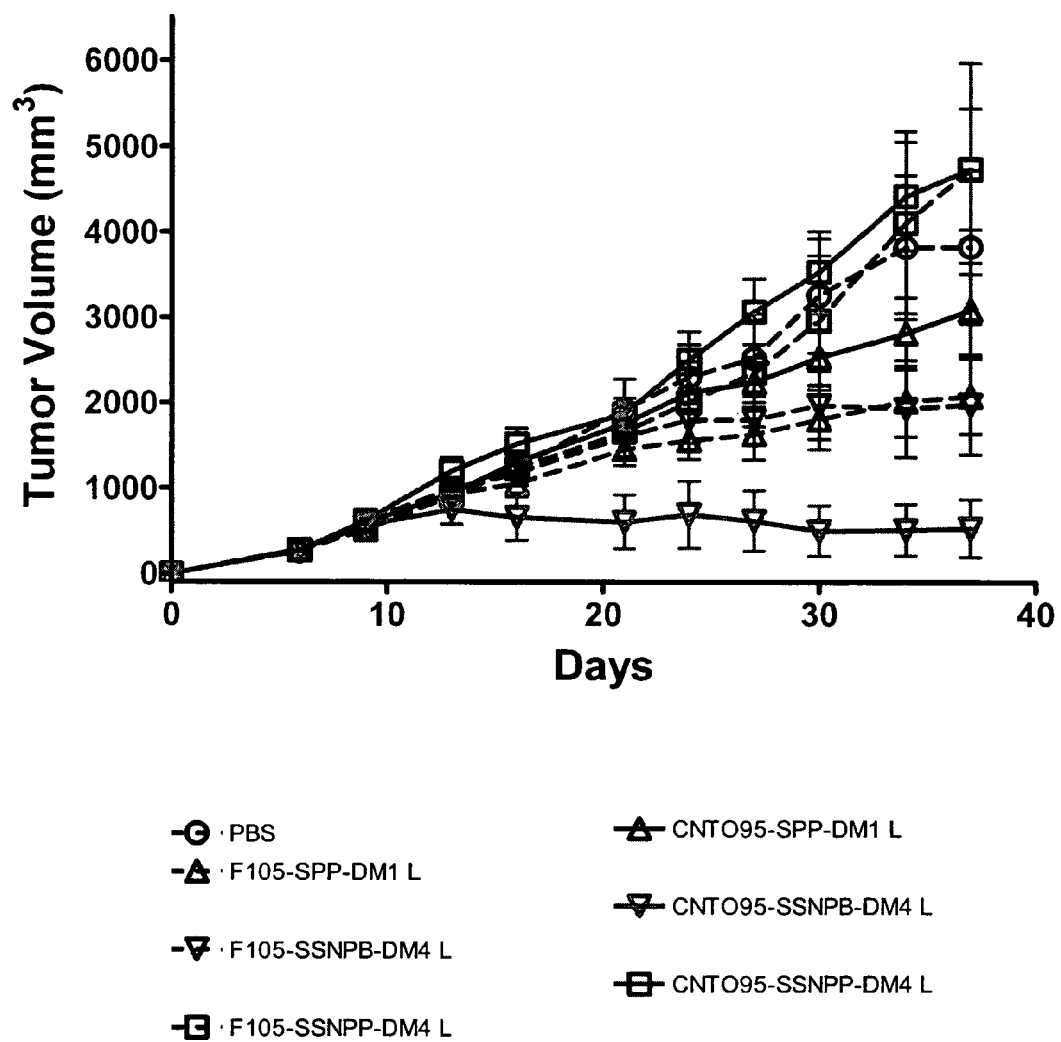
FIGS. 14A & B are graphs showing the change in mean tumor volume over time in rats bearing HT29 human colon tumor cells and treated with CNTO 364 (CNTO95-SPP-DM1), CNTO 365 (CNTO95-SSNPB-DM4), and CNTO 366 (CNTO95-SSNPP-DM4). A. PBS control and irrelevant antibody, F105, conjugated to the thiolated maytansines using the same process and reagents and injected on day 7 and 21 with 10 mg/kg. B. PBS control and conjugated antibodies as described injected at 20 mg/kg on day 7 and 21 except the CNTO365 group which received a single injection on day 7.
Figure 15A:
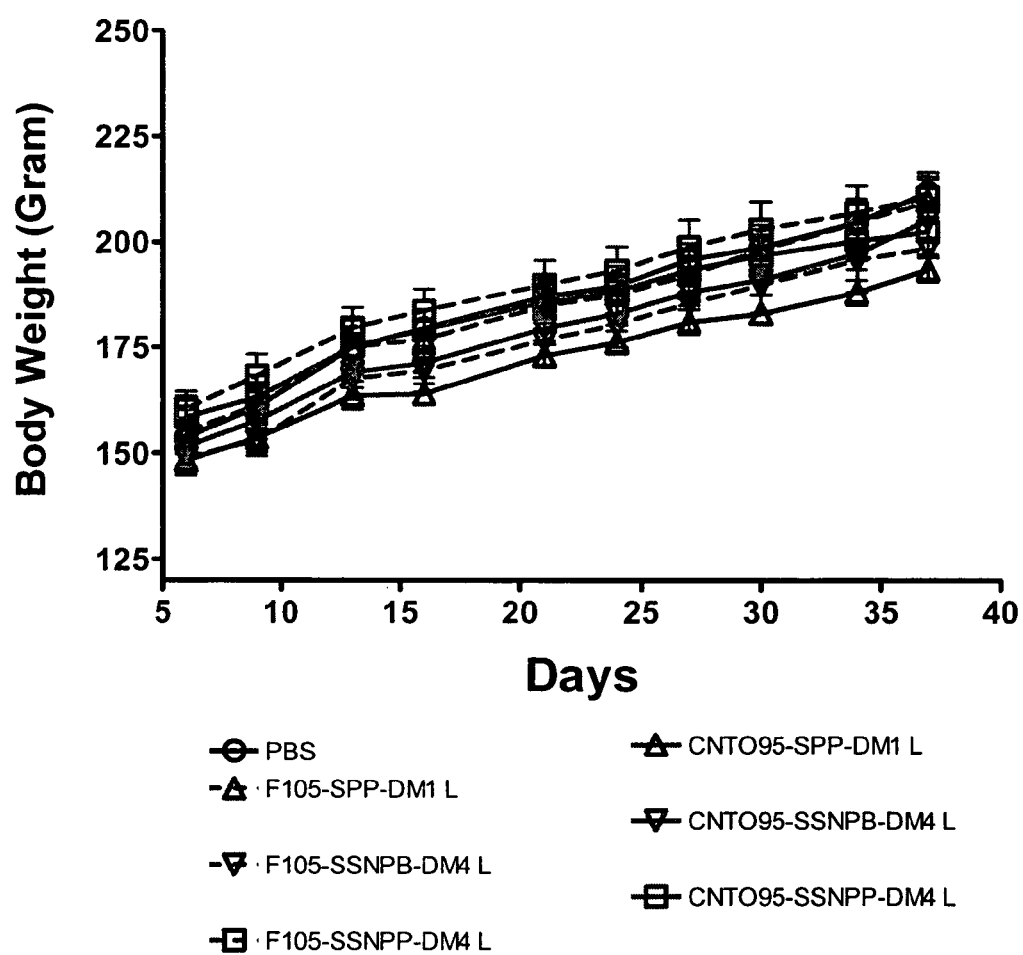
FIGS. 15A & B are graphs showing the mean change in body weight in rats bearing HT29 tumors as described in FIG. 14.
Figure 15B:
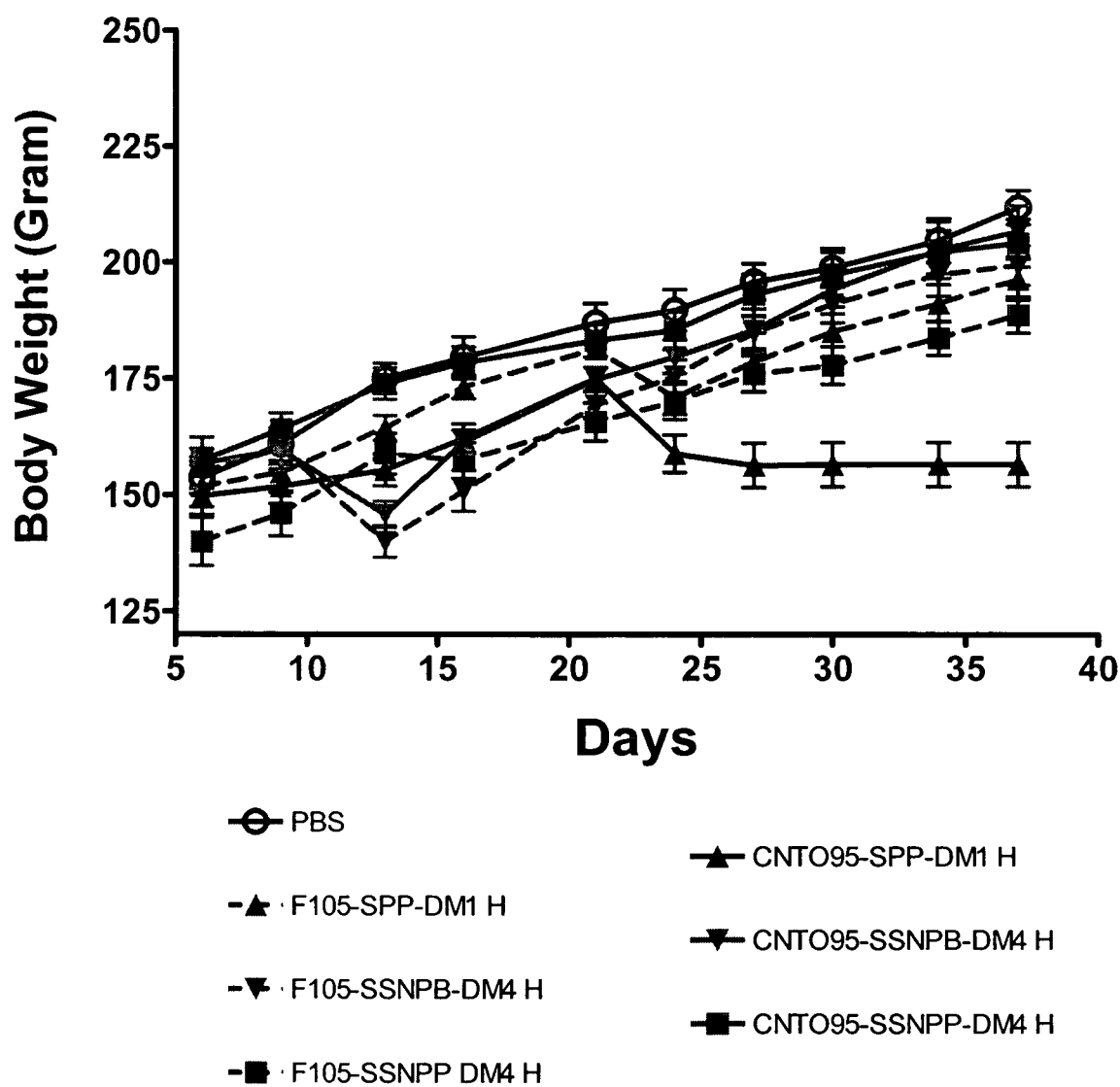

Human HT29 (ATCC) were cultured in αMEM supplemented with 10% FBS at 37° C. in the presence of 5% $CO_2$. Cells were prepared at a concentration of twenty-five million cells per ml in serum free αMEM for inoculation. Female athymic rats were inoculated with $5 \times 10^6$ HT29 cells subcutaneously (0.2 ml of $25 \times 10^6$ cells/ml) on the rear flank area (dorsal side, approximately 0.5 inches caudal to the last rib and 0.5 inches from the backbone). All rats were monitored twice per week for the appearance of tumor. The animals were stratified into 13 groups, 6 animals per group based on a mean tumor volume for each group of approximately 250 mm³. On the day of grouping (Day 7) each group received its initial dosing as listed in Table 11. Doses of immunoconjugates were calculated based on the contents of DM1 or DM4 in each conjugate. The L and H represent 175 and 350 µg/kg of DM1 or DM4, respectively. All test articles were given in a volume of 1 ml/100 gm of body weight. Except for group 11, which received only one dose on day 7, all other groups were dosed on day 7 and day 21. Changes in tumor volumes were used as indicators of potency (FIGS. 14A & B) and changes in body weight (FIGS. 15A & B) were used to monitor tolerability. All measurements are expressed as the group mean+/−SEM (n=6).

TABLE 11

| Group No | Ab conjugate administered (mg/kg) | Dose of DMx microgm/kg |
|---|---|---|
| 1. PBS | 0 | 0 |
| 2. F105-SPP-DM1 | 11.5 | DM1: 175 |
| 3. F105-SPP-DM1 | 23 | DM1: 350 |
| 4. F105-SSNPB-DM4 | 10 | DM4: 175 |
| 5. F105-SSNPB-DM4 | 20 | DM4: 350 |
| 6. F15-SSNPP-DM4 | 10.5 | DM4: 175 |
| 7. F105-SSNPP-DM4 | 21 | DM4: 350 |
| 8. CNTO 364 | 10 | DM1: 175 |
| 9. CNTO 364 | 20 | DM1: 350 |
| 10. CNTO 365 | 10 | DM4: 175 |
| 11. CNTO 365 | 20 | DM4: 350 |
| 12. CNTO 366 | 12 | DM4: 175 |
| 13. CNTO 366 | 24 | DM4: 350 |

Figure 14B:
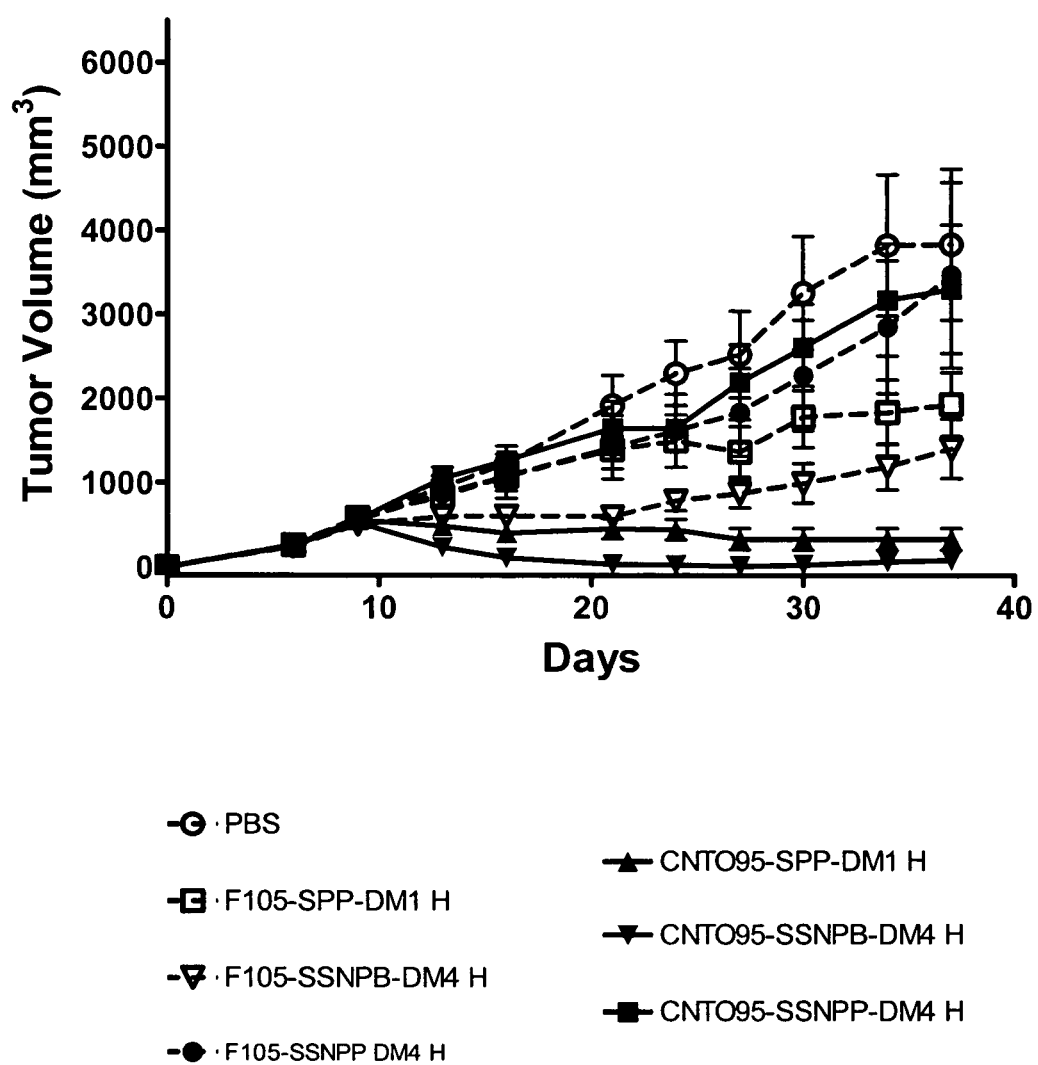

Animals injected with CNTO 365 and F105-SSNPB-DM4 at 350 microgm/kg of DM4 lost more than 10% of original body weight after the first dosing as shown in FIG. 14B. Therefore, dosing was discontinued in these two groups after one injection. The >10% body weight loss was transient and the animals recovered within 10 days of cessation of treatment. The remaining groups were dosed both on Day 7 and Day 21 and no significant body weight loss was observed except for the high dose CNTO 364 group, in which animals lost above 10% body weight. Significant weight loss had not been seen in other experiments using CNTO 364 on this dosing schedule. As shown in FIG. 14B, single injection of CNTO 365 at high dose caused complete regression of established sc human HT29 colon carcinoma in 4 out of 6 animals. CNTO 364 at high dose (350 microgm/kg of DM1) and CNTO 365 at low dose (175 microgm/kg of DM4) also regressed preformed colon tumors (2 out of 6 animals in each group respectively) or significantly inhibited the growth of HT29 colon tumors. However, CNTO 364 low dose (175 microgm/kg of DM1) and CNTO 366 at both doses did not have any significant effect on tumor sizes. These results suggest that CNTO 365 has better potency and efficacy than CNTO 364 and CNTO 366 when administered iv on a q14dx2 schedule in this tumor xenograft model.

It will be clear that the invention can be practiced otherwise than as particularly described in the foregoing description and examples.

Numerous modifications and variations of the present invention are possible in light of the above teachings and, therefore, are within the scope of the appended claims.

What is to be claimed:
1. An antibody-drug conjugate of the formula:

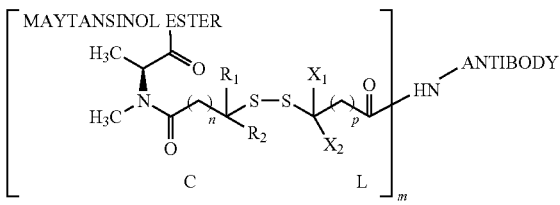

wherein the antibody is a human alphaV integrin specific antibody, and said antibody is capable of being internalized by a cell expressing said alphaV integrin, and wherein said antibody comprises (i) all of the heavy chain complementary determining region (CDR) amino acid sequences of CNTO 95 as shown in SEQ ID NOS: 1, 2, and 3, and (ii) all of the light chain CDR amino acid sequences of CNTO 95 as shown in SEQ ID NOS: 4, 5, and 6; and wherein the maytansinol is esterified at C-3; $R_1$ and $R_2$ are Me; $X_1$ and $X_2$ are H n is 2; p is 2; and m is 3-4, and the pharmaceutically acceptable salts and esters thereof.

2. An antibody conjugate according to claim 1, wherein the antibody molecule is specific for an epitope within the amino acid sequence SEQ ID NO: 9.

3. The antibody-drug conjugate of claim 1, wherein the antibody is a humanized or chimeric antibody.

4. A pharmaceutical composition comprising a conjugate according to claim 1 and a pharmaceutically acceptable carrier, diluent, or excipient.

5. An article of manufacture comprising the conjugate composition of claim 1 and a container, and further comprising a package insert or label indicating that the composition can be used to treat a disease characterized by cells expressing alphaV integrin.

6. An article of manufacture according to claim 5 wherein the package insert indicates that the composition can be used to treat cancer.

7. An antibody conjugate according to claim 1, wherein at least one of the heavy chain variable region sequences of the antibody comprises the heavy chain variable region sequence of CNTO 95 as shown in SEQ ID NO: 7.

8. An antibody conjugate according to claim 1, wherein at least one of the light chain variable region sequences of the antibody comprises the light chain variable region sequence of CNTO 95 as shown in SEQ ID NO: 8.

9. An antibody conjugate according to claim 1, wherein at least one of the heavy chain variable region sequences of the antibody comprises the heavy chain variable region sequence of CNTO 95 as shown in SEQ ID NO: 7 and at least one of the light chain variable region sequences of the antibody comprises the light chain variable region sequence of CNTO 95 as shown in SEQ ID NO: 8.

10. A method of production of an antibody-drug conjugate according to claim 1, comprising the steps: (a) introducing one or more free or protected thiol groups into the antibody by treating the antibody with a bifunctional coupling reagent represented by one of the following structural formulas:

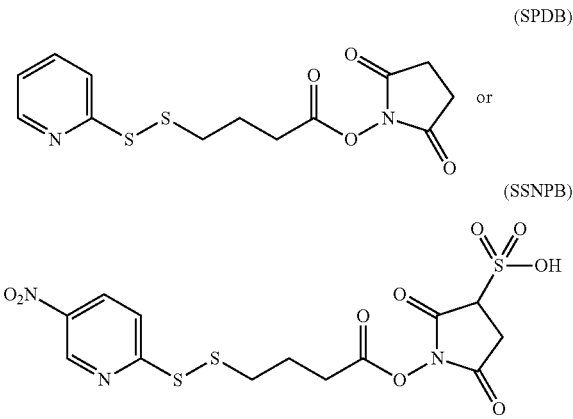

to form an activated antibody; (b) reacting the activated antibody with DM4 to form the antibody-drug conjugate; and (c) recovering the antibody-drug conjugate.

11. A method of treatment of cancer in a patient in need thereof comprising administering to the patient a therapeutically effective amount of a conjugate according to claim 1, wherein the cancer is lung adenocarcinoma or colon adenocarcinoma.

12. A method for inhibiting the growth of cancer cells in a mammal in need thereof comprising administering to the mammal a monoclonal antibody conjugate according to claim 1 in an amount effective to inhibit the growth of said cancer cells in said mammal, wherein the cancer is lung adenocarcinoma or colon adenocarcinoma.

13. The method according to claim 12, in which the antibody conjugate is administered intravenously.

14. The method according to claim 13, in which the antibody conjugate is administered in the amount of from 0.05 mg/kg to 12.0 mg/kg body weight.

15. The method according to claim 12, in which the mammal is a human patient.

* * * * *

UNITED STATES PATENT AND TRADEMARK OFFICE
CERTIFICATE OF CORRECTION

PATENT NO. : 8,603,483 B2
APPLICATION NO. : 11/290249
DATED : December 10, 2013
INVENTOR(S) : Chen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 29 days.

Signed and Sealed this
Twenty-third Day of May, 2017

Michelle K. Lee
*Director of the United States Patent and Trademark Office*